(12) United States Patent
Hajishah et al.

(10) Patent No.: US 11,969,380 B2
(45) Date of Patent: Apr. 30, 2024

(54) ADVANCED OCCLUSION MANAGEMENT METHODS FOR A PHACOEMULSIFICATION SYSTEM

(71) Applicant: Johnson & Johnson Surgical Vision, Inc., Irvine, CA (US)

(72) Inventors: Abraham Hajishah, Irvine, CA (US); Edith W. Fung, Diamond Bar, CA (US); Deep Mehta, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 332 days.

(21) Appl. No.: 15/724,997

(22) Filed: Oct. 4, 2017

(65) Prior Publication Data

US 2019/0099526 A1 Apr. 4, 2019

(51) Int. Cl.
*A61M 1/00* (2006.01)
*A61F 9/007* (2006.01)
*A61M 3/02* (2006.01)

(52) U.S. Cl.
CPC ...... *A61F 9/00745* (2013.01); *A61F 9/00736* (2013.01); *A61M 1/73* (2021.05);
(Continued)

(58) Field of Classification Search
CPC .. A61M 1/008; A61M 1/0058; A61M 1/0031; A61M 1/0066; A61M 1/0064; A61M 1/0076; A61M 2205/3331; A61M 2210/0612; A61M 2205/3351; A61M 2205/52; A61M 2205/3334; A61M 2205/505; A61M 2205/18; A61M 3/0283; A61M 2205/502; A61M 2205/3344; A61M 2205/3569; A61M 2205/50; A61M 1/84; A61M 1/74; A61M 1/774; A61F 9/00736; A61F 9/00745; A61F 9/007; A61B 2217/005

See application file for complete search history.

(56) References Cited

U.S. PATENT DOCUMENTS 3,393,566 A 7/1968 Malcolm et al.
3,920,014 A 11/1975 Banko
(Continued)

FOREIGN PATENT DOCUMENTS

EP 1382291 A2 1/2004
EP 1471342 A2 10/2004
(Continued)

OTHER PUBLICATIONS

International Search Report and Written Opinion for Application No. PCT/US2017/054602, dated Jan. 2, 2018, 10 pages.
(Continued)

*Primary Examiner* — Jessica Arble
(74) *Attorney, Agent, or Firm* — Johnson & Johnson Surgical Vision, Inc.

(57) ABSTRACT

The present invention provides a system for managing occlusions during phacoemulsification surgery. More specifically, the present invention provides a user of a surgical console an alert when a partial or full occlusion of a surgical tool causes the vacuum pressure to become greater than a predetermined pressure threshold setting and automatically reduces the vacuum pressure when the predetermined pressure threshold setting is exceeded.

45 Claims, 13 Drawing Sheets

(52) U.S. Cl.
CPC ............... *A61M 1/74* (2021.05); *A61M 1/77* (2021.05); *A61M 1/774* (2021.05); *A61M 1/80* (2021.05); *A61M 1/804* (2021.05); *A61B 2217/005* (2013.01); *A61M 1/72* (2021.05); *A61M 3/0201* (2021.05); *A61M 2205/18* (2013.01); *A61M 2205/3331* (2013.01); *A61M 2205/3334* (2013.01); *A61M 2205/3344* (2013.01); *A61M 2205/3351* (2013.01); *A61M 2205/3569* (2013.01); *A61M 2205/50* (2013.01); *A61M 2205/502* (2013.01); *A61M 2205/505* (2013.01); *A61M 2205/52* (2013.01); *A61M 2210/0612* (2013.01)

(56) References Cited

U.S. PATENT DOCUMENTS

| | | |
|---|---|---|
| 4,653,719 A | 3/1987 | Cabrera et al. |
| 4,702,733 A | 10/1987 | Wright et al. |
| 4,818,186 A | 4/1989 | Pastrone et al. |
| 4,832,685 A | 5/1989 | Haines |
| 4,935,005 A | 6/1990 | Haines |
| 4,954,960 A | 9/1990 | Lo et al. |
| 5,032,111 A | 7/1991 | Morris et al. |
| 5,047,009 A | 9/1991 | Morris et al. |
| 5,106,367 A | 4/1992 | Ureche et al. |
| 5,167,620 A | 12/1992 | Ureche et al. |
| 5,190,042 A | 3/1993 | Hock |
| 5,242,404 A | 9/1993 | Conley et al. |
| 5,354,268 A | 10/1994 | Peierson et al. |
| 5,405,269 A | 4/1995 | Stupecky |
| 5,417,246 A | 5/1995 | Perkins et al. |
| 5,476,448 A | 12/1995 | Urich |
| 5,487,827 A | 1/1996 | Peierson et al. |
| 5,569,188 A | 10/1996 | Mackool |
| 5,591,127 A | 1/1997 | Barwick, Jr. et al. |
| 5,616,120 A | 4/1997 | Andrew et al. |
| 5,649,905 A | 7/1997 | Zanger et al. |
| 5,695,473 A | 12/1997 | Olsen |
| 5,697,898 A | 12/1997 | Devine |
| 5,700,240 A | 12/1997 | Barwick, Jr. et al. |
| 5,733,256 A | 3/1998 | Costin |
| 5,766,146 A | 6/1998 | Barwick |
| 5,865,764 A | 2/1999 | Moorhead |
| 5,885,243 A | 3/1999 | Capetan et al. |
| 5,910,110 A | 6/1999 | Bastable |
| 5,935,106 A | 8/1999 | Olsen |
| 6,159,175 A | 12/2000 | Strukel et al. |
| 6,167,588 B1 | 1/2001 | Dyson |
| 6,179,808 B1 | 1/2001 | Boukhny et al. |
| 6,423,029 B1 | 7/2002 | Elsberry |
| 6,491,661 B1 | 12/2002 | Boukhny et al. |
| 6,533,747 B1 | 3/2003 | Polaschegg et al. |
| 6,565,535 B2 | 5/2003 | Zaias et al. |
| 6,579,255 B2 | 6/2003 | Kadziauskas et al. |
| 6,599,271 B1 | 7/2003 | Easley |
| 6,648,223 B2 | 11/2003 | Boukhny et al. |
| 6,740,058 B2 | 5/2004 | Lal et al. |
| 6,780,166 B2 | 8/2004 | Kanda et al. |
| 7,083,591 B2 | 8/2006 | Cionni |
| 7,297,137 B2 | 11/2007 | Gordon et al. |
| 7,785,336 B2 | 8/2010 | Staggs |
| 8,246,580 B2 | 8/2012 | Hopkins et al. |
| 8,380,126 B1 | 2/2013 | Ma et al. |
| 8,425,452 B2 | 4/2013 | Claus et al. |
| 8,430,841 B2* | 4/2013 | Claus ................. A61M 3/0283 604/118 |
| 8,523,812 B2 | 9/2013 | Boukhny et al. |
| 8,652,086 B2 | 2/2014 | Gerg et al. |
| 8,668,665 B2 | 3/2014 | Gerg et al. |
| 8,715,220 B2 | 5/2014 | Gerg et al. |
| 9,198,798 B2 | 12/2015 | Claus et al. |
| 9,482,563 B2 | 11/2016 | Calderin et al. |
| 9,549,851 B2 | 1/2017 | Chon et al. |
| 9,782,232 B1 | 10/2017 | Papac |
| 9,795,507 B2 | 10/2017 | Hajishah et al. |
| 9,861,522 B2 | 1/2018 | Sorensen et al. |
| 10,182,940 B2 | 1/2019 | Chandrakant et al. |
| 11,051,978 B2 | 7/2021 | Heeren et al. |
| 11,071,816 B2 | 7/2021 | Mehta et al. |
| 11,185,623 B2 | 11/2021 | Ovchinnikov et al. |
| 11,383,020 B2 | 7/2022 | Keh et al. |
| 2002/0019607 A1 | 2/2002 | Bui |
| 2003/0050619 A1 | 3/2003 | Mooijman et al. |
| 2003/0105437 A1 | 6/2003 | Neubert |
| 2004/0092885 A1 | 5/2004 | Duchon et al. |
| 2004/0092921 A1 | 5/2004 | Kadziauskas et al. |
| 2005/0054971 A1 | 3/2005 | Steen et al. |
| 2005/0080375 A1 | 4/2005 | Kadziauskas et al. |
| 2005/0096593 A1 | 5/2005 | Pope et al. |
| 2005/0118048 A1 | 6/2005 | Traxinger |
| 2005/0209560 A1* | 9/2005 | Boukhny ............ A61F 9/00745 604/118 |
| 2005/0209621 A1 | 9/2005 | Gordon et al. |
| 2005/0234441 A1 | 10/2005 | Bisch et al. |
| 2005/0261628 A1 | 11/2005 | Boukhny et al. |
| 2005/0261715 A1 | 11/2005 | Boukhny et al. |
| 2005/0267504 A1 | 12/2005 | Boukhny et al. |
| 2006/0058811 A1 | 3/2006 | Kishimoto et al. |
| 2006/0224107 A1 | 10/2006 | Claus et al. |
| 2006/0224143 A1 | 10/2006 | Claus et al. |
| 2007/0227265 A1 | 10/2007 | Sugi et al. |
| 2008/0033349 A1 | 2/2008 | Suzuki |
| 2008/0053560 A1 | 3/2008 | Hartman et al. |
| 2008/0112828 A1 | 5/2008 | Muri et al. |
| 2008/0319451 A1 | 12/2008 | Zacharias |
| 2009/0158855 A1 | 6/2009 | Holden |
| 2010/0130915 A1* | 5/2010 | Claus ................. A61F 9/00745 604/22 |
| 2010/0145302 A1 | 6/2010 | Cull et al. |
| 2010/0280435 A1* | 11/2010 | Raney ................. A61F 9/00745 604/22 |
| 2011/0152728 A1* | 6/2011 | Teodorescu ............ G16H 40/63 601/2 |
| 2011/0295191 A1 | 12/2011 | Injev |
| 2011/0313343 A1 | 12/2011 | Milutinovic et al. |
| 2012/0041362 A1 | 2/2012 | Gerg et al. |
| 2013/0131578 A1 | 5/2013 | Stalmans et al. |
| 2013/0150782 A1* | 6/2013 | Sorensen ............ A61F 9/00745 604/319 |
| 2013/0246079 A1 | 9/2013 | Hoffman et al. |
| 2014/0114236 A1 | 4/2014 | Gordon et al. |
| 2014/0114237 A1 | 4/2014 | Gordon et al. |
| 2014/0163455 A1 | 6/2014 | Wilson et al. |
| 2014/0171869 A1 | 6/2014 | Zhang |
| 2014/0257172 A1 | 9/2014 | Yalamanchili et al. |
| 2014/0282018 A1 | 9/2014 | Amble et al. |
| 2014/0323953 A1* | 10/2014 | Sorensen ............ A61F 9/00745 604/28 |
| 2014/0364799 A1 | 12/2014 | Beauvais et al. |
| 2015/0057524 A1 | 2/2015 | Artsyukhovich et al. |
| 2016/0220751 A1 | 8/2016 | Mallough et al. |
| 2016/0346123 A1 | 12/2016 | Koplin |
| 2016/0367735 A1 | 12/2016 | Eddo et al. |
| 2017/0022488 A1 | 1/2017 | Bermudez et al. |
| 2017/0224888 A1 | 8/2017 | Hickey et al. |
| 2017/0246419 A1 | 8/2017 | Callaghan et al. |
| 2017/0333253 A1 | 11/2017 | Heeren et al. |
| 2018/0028359 A1 | 2/2018 | Gordon et al. |
| 2018/0049220 A1 | 2/2018 | Patil et al. |
| 2018/0049920 A1 | 2/2018 | Charles |
| 2018/0078415 A1 | 3/2018 | Citterio et al. |
| 2018/0092774 A1 | 4/2018 | Mehta et al. |
| 2018/0296738 A1 | 10/2018 | King et al. |
| 2018/0318131 A1 | 11/2018 | Boukhny et al. |
| 2019/0099547 A1 | 4/2019 | Mehta et al. |
| 2019/0133822 A1 | 5/2019 | Banko |
| 2021/0106734 A1 | 4/2021 | Mehta et al. |
| 2021/0153741 A1 | 5/2021 | Berdahl et al. |
| 2021/0353145 A1 | 11/2021 | Kamthan et al. |

(56) References Cited

U.S. PATENT DOCUMENTS

| | | |
|---|---|---|
| 2021/0386927 A1 | 12/2021 | Mehta et al. |
| 2021/0386928 A1 | 12/2021 | Mehta et al. |

FOREIGN PATENT DOCUMENTS

| | | |
|---|---|---|
| EP | 1471342 B1 | 8/2009 |
| EP | 2379126 A2 | 10/2011 |
| EP | 2164435 B1 | 8/2012 |
| JP | 62500640 T | 3/1987 |
| JP | 2001161740 A2 | 6/2001 |
| WO | 9945868 A1 | 9/1999 |
| WO | 03047653 A1 | 6/2003 |
| WO | 04108189 A2 | 12/2004 |
| WO | 04110524 A2 | 12/2004 |
| WO | 05037156 A1 | 4/2005 |
| WO | 2008030872 A1 | 3/2008 |
| WO | 2011045033 A1 | 4/2011 |
| WO | 2011105909 A1 | 9/2011 |
| WO | 2016122790 A1 | 8/2016 |
| WO | 2016148754 A1 | 9/2016 |
| WO | 2016150754 A1 | 9/2016 |
| WO | 2016191665 A1 | 12/2016 |
| WO | 2017044138 A1 | 3/2017 |
| WO | 2021083938 A1 | 5/2021 |

OTHER PUBLICATIONS

International Search Report and Written Opinion for Application No. PCT/IB2018/057689, dated Jan. 24, 2019, 16 pages.

International Search Report and Written Opinion for Application No. PCT/IB2018/057699, dated Jan. 30, 2019, 15 pages.

Partial International Search Report for Application No. PCT/IB2018/057580, dated Jan. 23, 2019, 15 pages.

International Search Report and Written Opinion for Application No. PCT/IB2018/057494, dated Dec. 19, 2018, 13 pages.

International Search Report and Written Opinion for Application No. PCT/IB2018/057574, dated Dec. 14, 2018, 16 pages.

Cionni R.J., "Evaluating Two Key Safety Advances In the Centurion Vision System", ALCON, Cataract and Refractive Surgery Today, Aug. 2019, 4 pages.

Gopesh T., et al., "Rapid and Accurate Pressure Sensing Device for Direct Measurement of Intraocular Pressure", Translational Vision Science and Technology (TVST), Feb. 2020, vol. 9 (3), Article 28, pp. 1-9.

Bello S., et al., Development of a Smart Pump for Monitoring and Controlling Intraocular Pressure, Annals of Biomedical Engineering, Apr. 2017, vol. 45(4), pp. 990-1002.

* cited by examiner

| Name | Max Power | Max Aspiration (ccm) | Vacuum Range (mmHg) |
|---|---|---|---|
| Normal State | 35% | 20 | 0 to 246 |
| Weak Occlusion | 55% | 45 | 246 to 370 |
| Strong Occlusion | 45% | 30 | 370 to 390 |

FIG. 7B

ADVANCED OCCLUSION MANAGEMENT METHODS FOR A PHACOEMULSIFICATION SYSTEM

BACKGROUND

Field of Invention

The present disclosure relates generally to medical apparatuses and methods that provide pressurized infusion of liquids for ophthalmic surgery, and more particularly, to medical apparatuses and methods that require determinable, stable or controlled intraocular pressure (TOP) within the anterior chamber of the eye.

Description of Related Art

During ophthalmic surgery, an ophthalmic surgical apparatus is used to perform surgical procedures in a patient's eye. An ophthalmic surgical apparatus typically includes a handheld medical implement or tool, such as a handpiece with a tip and/or sleeve, and operating controls for regulating settings or functions of the apparatus and tool. Operation of the tool requires control of various operating settings or functions based on the type of tool used. Such apparatuses typically include a control module, power supply, an irrigation source, one or more aspiration pumps, as well as associated electronic hardware and software for operating a multifunction handheld surgical tool. The handpiece may include a needle or tip which is ultrasonically driven once placed with the incision to, for example, emulsify the lens of the eye. In various surgical procedures, these components work together in order to, for example, emulsify eye tissue, irrigate the eye with a saline solution, and aspirate the emulsified lens from the eye.

An exemplary type of ophthalmic surgery is phacoemulsification. Phacoemulsification includes making a corneal and/or scleral incision and the insertion of a phacoemulsification handpiece that includes a needle or tip that is ultrasonically driven to emulsify, or liquefy, the lens. A phacoemulsification system typically includes a handpiece coupled to an irrigation source and an aspiration pump. The handpiece includes a distal tip that emits ultrasonic energy to emulsify a crystalline lens within the patient's eye. The handpiece includes one or more irrigation ports proximal to the distal tip and coupled to the irrigation source via an irrigation input line. The handpiece further includes an aspiration port at the distal tip that is coupled to the aspiration pump via an aspiration output line. Concomitantly with the emulsification, fluid from the irrigation source (which may be a bottle or bag of saline solution that is elevated above the patient's eye, to establish positive pressure by gravity, and/or with external pressure source) is irrigated into the eye via the irrigation line and the irrigation port(s). This fluid is directed to the crystalline lens in the patient's eye in order to maintain the anterior chamber and capsular bag and replenish the fluid aspirated away with the emulsified crystalline lens material. The irrigation fluid in the patient's eye and the crystalline lens material is aspirated or removed from the eye by the aspiration pump and line via the aspiration port. In some instances, the aspiration pump may be in the form of, for example, a peristaltic or positive displacement pump. Other forms of aspiration pumps are well known in the art, such as vacuum pumps. In addition, more than one pump or more than one type of pump may be used. Additionally, some procedures may include irrigating the eye and aspirating the irrigation fluid without concomitant destruction, alteration or removal of the lens.

Intraocular pressure (TOP) is the fluid pressure inside the anterior chamber of the eye. In a normal eye, intraocular pressure may vary depending on the time of day, activities of the patient, fluid intake, medications, etc. Intraocular pressure may be measured as static (a specific value) or dynamic (a range of values). It is well known that the IOP in an anterior chamber of the eye is required to be controlled and maintained during such surgical procedures in order to avoid damage to the patient's eye.

Different medically recognized techniques have been utilized for ophthalmic surgery, such as phacoemulsification, in order to maintain and control the IOP of a patient's eye. In various examples, phacoemulsification may involve combining irrigation, aspiration and emulsification within a single handpiece. The handpiece that is typically controlled electrically in order to, for example, control the flow of fluid through the handpiece and tip. As may be appreciated, during a surgical procedure, the flow of fluid to and from a patient's eye (through a fluid infusion/irrigation system or aspiration/extraction system, for example), the fluid pressure flowing through the handpiece, and the power control over the handpiece, are all critical to the procedure performed. Precise control over aspiration and irrigation to the ocular region is desired in order maintain a desired or optimal IOP within the anterior chamber of the eye. Similarly, it may be necessary to maintain a stable volume of liquid in the anterior chamber of the eye, which may be accomplished by irrigating fluid into the eye at the same rate as aspirating fluid and lens material from the eye.

In prior ophthalmic surgical devices, the control and settings of the system may be electronically controlled or modified by use of a computer system, control module and/or a user/surgeon. For instance, the control module may also provide feedback information to a user or surgeon regarding the function and operation of the system, or may also receive input from a user or surgeon in order to adjust surgical settings. A surgeon or user may interface with a display system of the control module during use of the device.

Additionally, a surgeon or user may control or adjust certain aspects of the IOP by adjusting various settings or functions of the system. For instance, the irrigation source may be in the form of a suspended or lifted saline bottle or bag, and the surgeon is typically able to adjust the height of the bottle or bag to create a specific head height pressure of the fluid flowing from the bottle or bag. In typical systems, the head height pressure, which is a function of the column height, is the static IOP of the fluid flowing through the patient's eye. Accordingly, the surgeon may be able to indirectly set the static IOP by changing the bottle height to a desired level. However, dynamic IOP is a function of surgical parameters and the surgical environment during surgery. Currently, ophthalmic systems do not provide any means for measuring or predicting dynamic IOP.

Even further, prior phacoemulsification systems do not provide a process to manage IOP during post occlusion surge thereby affecting anterior chamber stability. Further, prior phacoemulsification systems do not provide any indication of occlusion or post occlusion surge events.

Current phacoemulsification systems, both based on peristaltic and Venturi systems may not provide suitable methods of managing IOP during post occlusion surge, often resulting in uncontrolled changes to the stability of the anterior chamber. More specifically, current Venturi based systems, including those using a gravity based infusion system, may not provide any indication(s) relative to post occlusion surge events. For example, if a phacoemulsification needle tip is occluded with cataract material, a high vacuum state may be created within the outflow tubing. This high vacuum level may at least partially collapse the walls of the elastic tubing, and, once the occlusion breaks, the walls of the tubing may rebound back into shape, rapidly pulling fluid from the eye and creating a surge. Because the volume of the anterior and posterior chambers are so small, a slight collapse in the length of the long outflow tubing may create a significant surge and increase the risk for collapse of the eye and aspiration of the posterior capsule during surgery. Thus, the management and quantification of TOP and occlusion, and post occlusion surge detection, may provide improved fluidics control during phacoemulsification surgery and may lead to better surgical outcomes by improving anterior chamber stability and more reliable surgical systems.

SUMMARY

The present invention provides a method for managing occlusions during phacoemulsification surgery. The method may comprise providing, by a surgical console having at least one system bus communicatively connected to at least one computing processor capable of accessing at least one computing memory associated with the at least one computing processor, a vacuum system capable of providing vacuum pressure between a minimum pressure and a maximum pressure, receiving a first pressure threshold setting and a second pressure threshold setting, wherein the first pressure threshold setting is greater than the minimum pressure and less than the second pressure threshold setting and wherein the second pressure threshold setting is less than the maximum pressure, providing a user of the surgical console an alert in response to the vacuum pressure being greater than the first pressure threshold setting, and automatically reducing the vacuum pressure in response to the second pressure threshold setting being exceeded.

The present invention also provides a system for managing occlusions during phacoemulsification surgery. The system comprises a surgical console having at least one system bus communicatively connected to at least one computing processor capable of accessing at least one computing memory associated with the at least one computing processor, at least one vacuum source associated with the surgical console for providing a vacuum pressure between a minimum pressure and a maximum pressure, a phacoemulsification surgical handpiece having at the distal end at least one surgical tool and having near the proximate end a receiver for receiving an aspiration line from the surgical console, and an input means for receiving a first pressure threshold setting and a second pressure threshold setting, wherein the first pressure threshold setting is greater than the minimum pressure and less than the second pressure threshold setting and wherein the second pressure threshold setting is less than the maximum pressure, wherein the surgical console provides a user of the surgical console an alert when the vacuum pressure is greater than the first pressure threshold setting and automatically reduces the vacuum pressure when the second pressure threshold setting exceeded.

The present invention also provides a method for managing occlusions during phacoemulsification surgery by providing, through a surgical console having at least one system bus communicatively connected to at least one computing processor capable of accessing at least one computing memory associated with the at least one computing processor, a vacuum system comprising three regions capable of providing vacuum pressure between a minimum pressure and a maximum pressure. The system may receive a first pressure threshold setting and a second pressure threshold setting, wherein the first pressure threshold setting is greater than the minimum pressure and less than the second pressure threshold setting and wherein the second pressure threshold setting is less than the maximum pressure, wherein the three regions capable of providing vacuum pressure are normal state, weak occlusion state, and strong occlusion state and wherein each of the three regions possess respective settings comprising power, pressure, and pressure threshold and wherein the normal state is between the minimum pressure and the first pressure threshold, the weak-occlusion state is between the first pressure threshold and the second pressure threshold, and the strong occlusion state is between the second pressure threshold and the maximum pressure. The system may also display, on a graphical user interface, current aspiration, vacuum, and power settings.

BRIEF DESCRIPTION OF THE DRAWINGS

The organization and manner of the structure and function of the disclosure, together with the further objects and advantages thereof, may be understood by reference to the following description taken in connection with the accompanying drawings, and in which:

FIG. 7B is a chart illustrative of an embodiment of the present invention;

DETAILED DESCRIPTION

The following description and the drawings illustrate specific embodiments sufficiently to enable those skilled in the art to practice the described system and method. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

Figure 1:
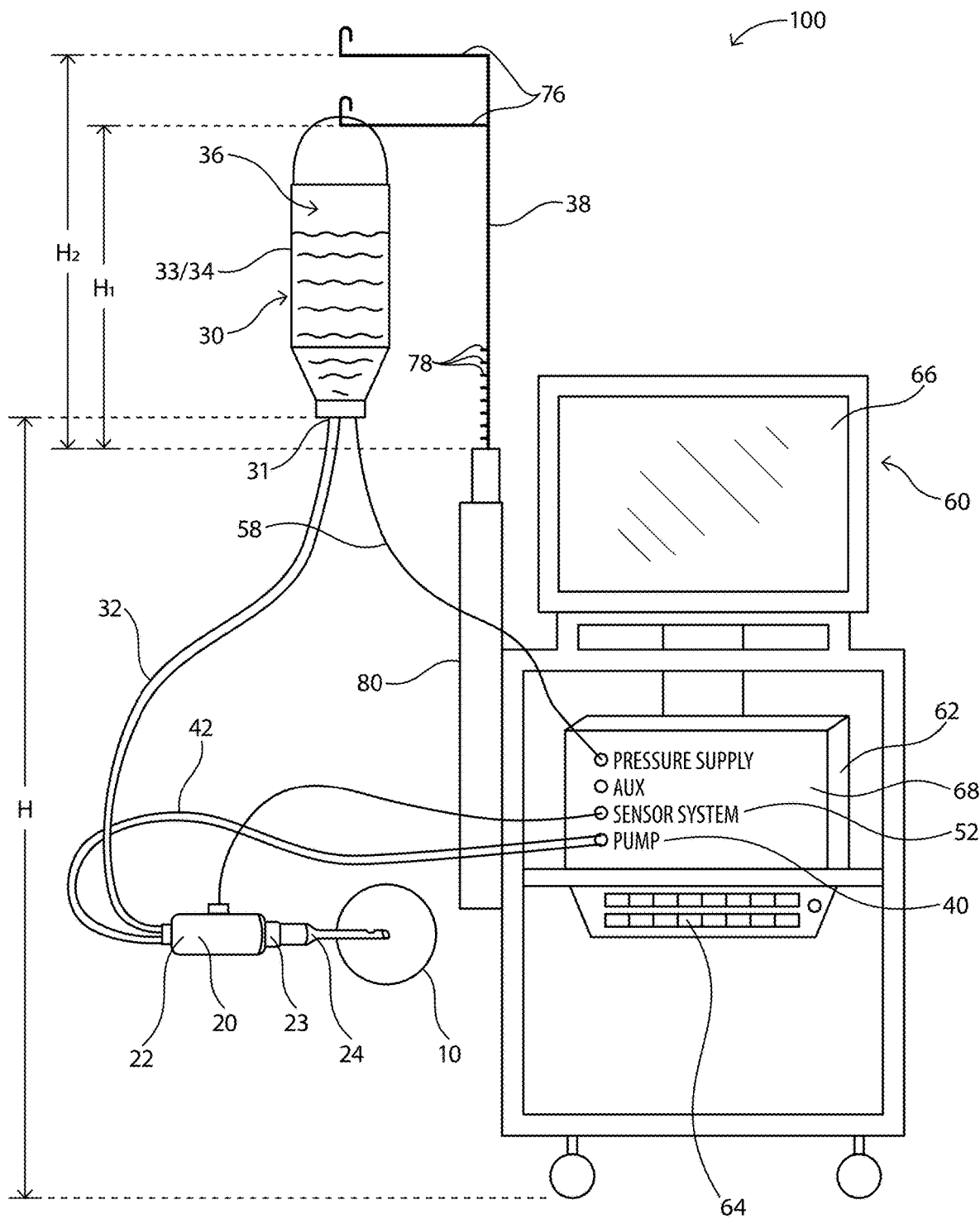
FIG. 1 illustrates a diagram of an exemplary phacoemulsification/diathermy/vitrectomy system in accordance with the present disclosure, the system including a control module to control various features of the system.
Figure 2:
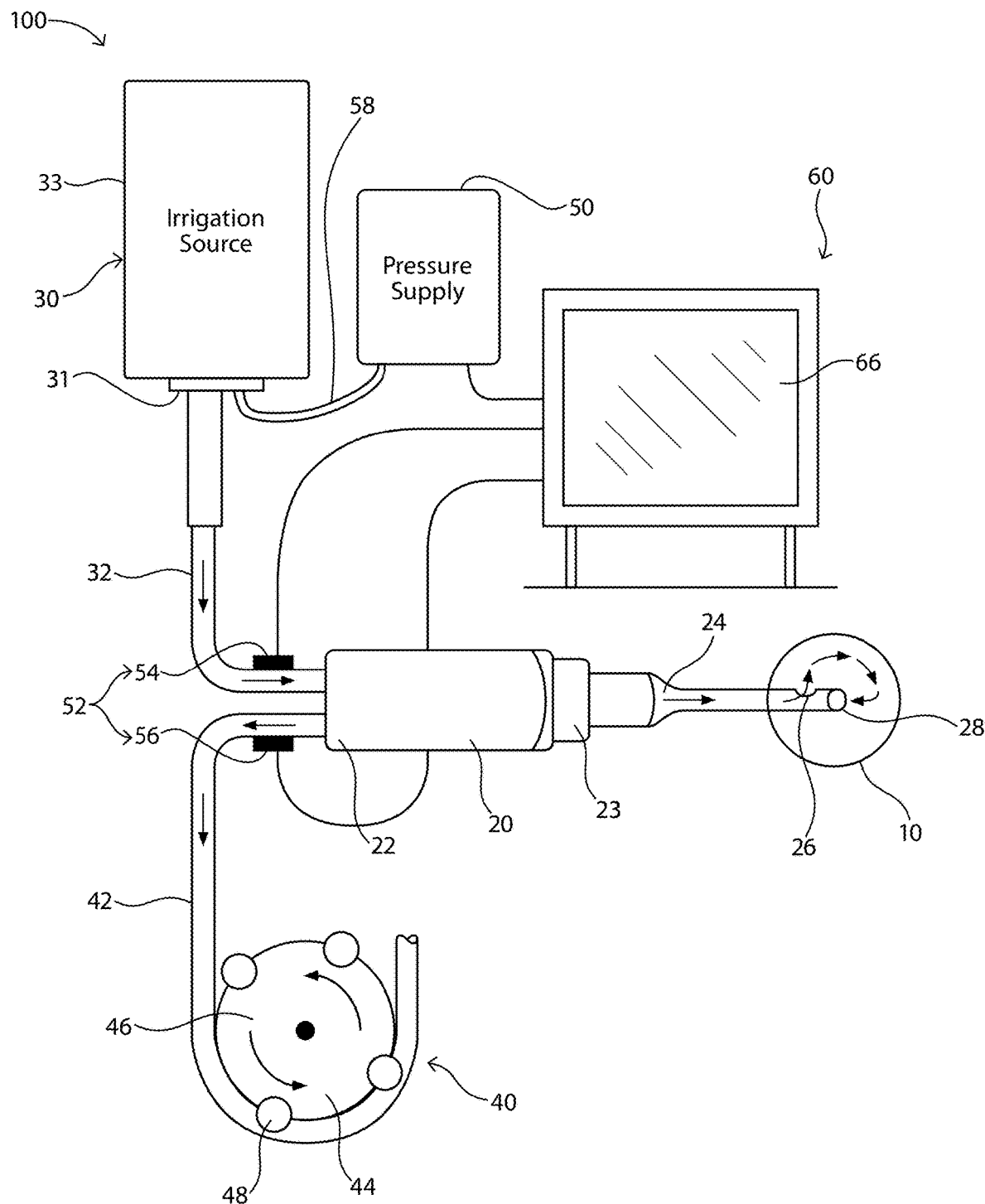
FIG. 2 illustrates an alternative phacoemulsification/diathermy/vitrectomy system and illustrated connected to various components of the system in order to determine characteristics or features of the components.

FIGS. 1 and 2 illustrate an exemplary phacoemulsification/diathermy/vitrectomy system 100. As illustrated, the system 100 includes, for example, a handpiece or wand 20 having a distal end 23 configured to receive an interchangeable tip 24 and a proximate end 22. The system 100 further includes an irrigation source 30, an aspiration source 40, an optional pressure supply 50, and a control module 60. In illustrative embodiments, fluid is controllably directed through the system 100 in order to irrigate a patient's eye, illustrated representatively at 10, during an ocular surgical procedure. Various embodiments of the handpiece 20, irrigation source 30, aspiration source 40, optional pressure supply 50 and control module 60 are well known in the art and are embodied in this disclosure.

As illustrated in FIGS. 1 and 2, the irrigation source 30 is configured to supply a predetermined amount of fluid to the handpiece 20 for use during a surgical operation. Such fluid is supplied in order to, for example, stabilize or maintain a certain TOP in the anterior chamber of the eye during surgery, as well as provide means for fluidly transporting any particles (e.g. lens particulates that are created during emulsification) out of the eye. Various aspects (e.g. the flow rate, pressure) of fluid flow into and out of the anterior chamber of the eye will typically affect the operations of the surgical procedure and in particular the TOP measurements of the anterior chamber of the eye during the surgical procedure.

In illustrative embodiments, fluid may flow from the irrigation source 30 to the handpiece 20 via an irrigation line 32. The irrigation source 30 may be any type of irrigation source 30 that can create and control a constant fluid flow. In illustrative embodiments, the irrigation source is elevated to a predetermined height H via an extension arm 38. The extension arm 38 having two horizontal arms 76 on which the irrigation source 30 can be placed. The two horizontal arms 76 being elevated to predetermined heights $H_1$ and $H_2$. The predetermined heights $H_1$ and $H_2$ being adjustable by biased retaining members 78 attached to extension arm 38. The biased retaining members 78 being capable of adjustment by fixed receiver 80. In illustrative embodiments, the irrigation source 30 may be configured to be an elevated drip bag 33/34 that supplies a steady state of fluid 36 to the irrigation line 32. The irrigation line 32 being connected by exit port 31 to the elevated drip bag 33/34. The pressure supply 50 may be coupled to the irrigation source 30 in order to maintain a constant pressure in the irrigation source 30 as fluid exits the irrigation source 30, as is known in the industry. Other embodiments of a uniform irrigation source are well known in the art.

During the surgical procedure, it is typically necessary to remove or aspirate fluid and other material from the eye. Accordingly, fluid may be aspirated from the patient's eye, illustrated representatively at 10, via the handpiece 20 to flow through an aspiration line 42 to the aspiration source 40. The aspiration source 40 may be any type of aspiration source 40 that aspirates fluid and material from the eye. In illustrative embodiments, the aspiration source 40 may be configured to be a flow-based pump 44 (such as a peristaltic pump) or a vacuum-based pump (such as a Venturi pump) that are well known in the art. The aspiration source 40 may create a vacuum system to pump fluid and/or material out of the eye via the aspiration line 42. Other embodiments of an aspiration source are well known in the art.

The irrigation port 26 is fluidly coupled to the irrigation line 32 to receive fluid flow from the irrigation source 30, and the aspiration port 28 is fluidly coupled to the aspiration line 42 to receive fluid and/or material flow from the eye. The handpiece 20 and the tip 24 may further emit ultrasonic energy into the patient's eye, for instance, to emulsify or break apart the crystalline lens within the patient's eye. Such emulsification may be accomplished by any known methods in the industry, such as, for example, a vibrating unit (not shown) that is configured to ultrasonically vibrate and/or cut the lens, as is known in the art. Other forms of emulsification, such as a laser, are well known in the art. Concomitantly with the emulsification, fluid from the irrigation source 30 is irrigated into the eye via the irrigation line 32 and the irrigation port 26. During and after such emulsification, the irrigation fluid and emulsified crystalline lens material are aspirated from the eye by the aspiration source 40 via the aspiration port 28 and the aspiration line 42. Other medical techniques for removing a crystalline lens also typically include irrigating the eye and aspirating lens parts and other liquids. Additionally, other procedures may include irrigating the eye and aspirating the irrigating fluid within concomitant destruction, alternation or removal of the lens.

The aspiration source 40 is configured to aspirate or remove fluid and other materials from the eye in a steady, uniform flow rate. Various means for steady, uniform aspiration are well known in the art. In illustrative embodiments, the aspiration source 40 may be a Venturi pump, a peristaltic pump, or a combined Venturi and peristaltic pump. In illustrative embodiments, and as shown in FIG. 2, a peristaltic pump 44 may be configured to include a rotating pump head 46 having rollers 48. The aspiration line 42 is configured to engage with the rotating pump head 46 as it rotates about an axis. As the pump head 46 rotates the rollers 48 press against the aspiration line 42 causing fluid to flow within the aspiration line 42 in a direction of the movement for the rollers 48. Accordingly, the pump 44 directly controls the volume or rate of fluid flow, and the rate of fluid flow can be easily adjusted by adjusting the rotational speed of the pump head 46. Other means of uniformly controlling fluid flow in an aspiration source 40 are well known in the art. When the aspiration source 40 includes a combined Venturi and peristaltic pump, the aspiration source 40 may be controlled to automatically switch between the two types of pumps or user controlled to switch between the two types of pumps.

In illustrative embodiments, the control module 60 is configured to monitor and control various components of the system 100. For instance, the control module 60 may monitor, control, and provide power to the pressure supply 50, the aspiration source 40, and/or the handpiece 20. The control module 60 may be in a variety of forms as known in the art. In illustrative embodiments, the control module 60 may include a microprocessor computer 62, a keyboard 64, and a display or screen 66, as illustrated in FIGS. 1 and 2. The microprocessor computer 62 may be operably connected to and control the various other elements of the system, while the keyboard 64 and display 66 permit a user to interact with and control the system components as well.

In an embodiment a virtual keyboard on display 66 may be used instead of keyboard 64. In illustrative embodiments, the control module 60 may also include a pulsed ultrasonic power source (not shown) that can be controlled by the computer 62 in accordance with known methods or algorithms in the art. A system bus 68 may be further provided to enable the various elements to be operable in communication with each other.

The screen 66 may display various measurements, criteria or settings of the system 100 such as the type of procedure, the phase of the procedure and duration of the phase, various parameters such as vacuum, flow rate, power, and values that may be input by the user, such as bottle height, sleeve size, tube length (irrigation and aspiration), tip size, vacuum rate. The screen 66 may be in the form of a graphical user interface (GUI) associated with the control module 60 and utilizing a touchscreen interface, for example. The GUI may allow a user to monitor the characteristics of the system 100 or select settings or criteria for various components of the system. For instance, the GUI may permit a user to select or alter the maximum pressure being supplied by the pressure supply 50 to the irrigation source 30 via line 58. The user may further control the operation of the phase of the procedure, the units of measurement used by the system 100, or the height of the irrigation source 30, as discussed below. The GUI may further allow for the calibration and priming of the pressure in the irrigation source 30.

In illustrative embodiments, the system 100 may include a sensor system 52 configured in a variety of ways or located in various locations. For example, the sensor system 52 may include at least a first sensor or strain gauge 54 located along the irrigation line 32 and a second sensor or strain gauge 56 located along the aspiration line 42, as illustrated in FIG. 2. Other locations for the sensors 54 and 56 are envisioned anywhere in the system 100, e.g. on the handpiece 20, and may be configured to determine a variety of variables that may be used to determine TOP measurements in the eye, as discussed below. This information may be relayed from the sensor system 52 to the control module 60 to be used in the determination of TOP measurements. The sensor system 52 may also include sensors to detect other aspects of the components used in the system, e.g. type of pump used, type of sleeve used, gauge of needle tip (size), etc.

Those of skill in the art will recognize that any step of a method described in connection with an embodiment may be interchanged with another step without departing from the scope of the invention. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Any options available for a particular medical device system may be employed with the present invention. For example, with a phacoemulsification system the available settings may include, but are not limited to, irrigation, aspiration, vacuum level, flow rate, pump type (flow based and/or vacuum based), pump speed, ultrasonic power (type and duration, e.g. burst, pulse, duty cycle, etc.), irrigation source height adjustment, linear control of settings, proportional control of settings, panel control of settings, and type (or "shape") of response.

In illustrative embodiments, the interface provides feedback to the user should the pre-determined or automatic settings, variables, or criteria need adjustment to ensure all the desired settings of the system. The interface can then permit the user to change or modify those settings accordingly.

Other mechanisms for setting and/or programming a particular setting may be employed with the present invention, including, but not limited to, clicking on an icon on a display screen using a mouse or touch screen depressing a button/switch on a foot pedal, voice activated commands and/or combinations thereof.

In an embodiment of the present invention, irrigation and/or aspiration vacuum at, or in near proximity to, the phacoemulsification hand piece may be measured in real time. Existing phacoemulsification handpieces do not provide a method to measure pressure on or within the irrigation and/or aspiration lines. Measuring pressure on the irrigation and/or aspiration lines in close proximity to the phacoemulsification handpiece may allow for more accurate and precise estimations of the pressures at the surgical site, such as in, for example, a patient's anterior chamber of the eye. More accurate pressure and vacuum measurements, for example, may be utilized to develop algorithms to provide more robust fluidics control during phacoemulsification surgery which may lead to the improvement of anterior chamber stability. This, in turn, may provide additional comfort to the patient, control over the surgical parameters to the operating surgeon, and ensure safer operation of peristaltic and/or Venturi based pumps during phacoemulsification surgery.

In an embodiment of the present invention, an in-line irrigation pressure sensor and aspiration vacuum sensor may be located on or proximate to the hand piece may provide real-time irrigation and aspiration vacuum data. The proximity of pressure sensors to the surgical site during phacoemulsification surgery may allow for increased monitoring of, for example, the anterior chamber environment. Data collected from one or more of the sensors may allow for the development of an algorithm which may be used to monitor intraocular pressure, and predict occlusion and post occlusion surge events during surgery more accurately and in a more timely manner than is currently available. Using the developed algorithm, discussed herein below, the system may adjust the irrigation and/or aspiration rates in order to improve, for example, anterior chamber stability. Similarly, when the aspiration slows down, fluid circulation may recede and the heat generated from the handpiece tip may damage the eye's tissues, which is not desirable.

Figure 3:
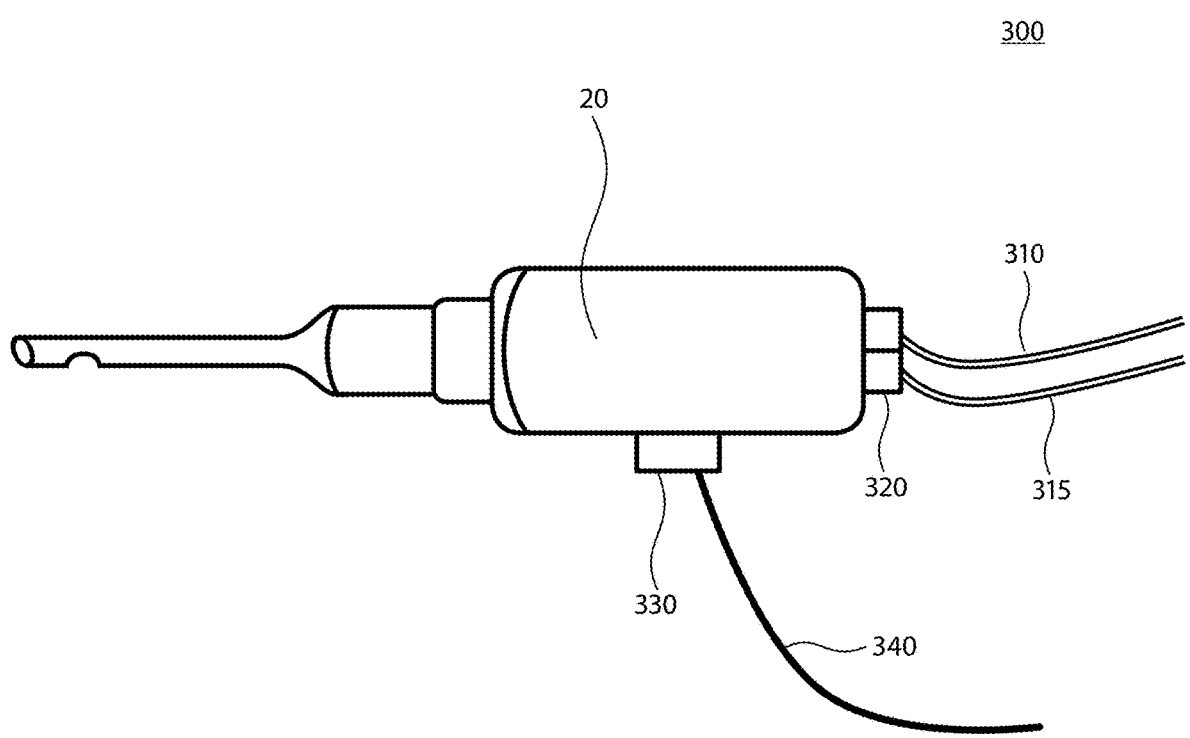
FIG. 3 illustrates an alternative aspect of the phacoemulsification/diathermy/vitrectomy system.

As illustrated in handpiece system 300 of FIG. 3, at least one sensor module 320 may be placed in proximity to the phacoemulsification handpiece. Such a module may include a pressure sensor in communication with irrigation line 32 as well as a pressure sensor in communication with the aspiration line 42. The sensor module 320 may receive power and transmit sensor measurement data over power and data pins located in the communication module 330 located on the handpiece 20. The communication module 330 may operate on a specific voltage, for example, and may transmit measurements to the console and or system via a wireless or wired connection.

As illustrated in FIG. 3, the module may receive power from the console or other aspect associated with the console through cable 340 and may similarly transmit data through cable 340. In an embodiment of the present invention, the handpiece system 300 may transmit sensor and other data wirelessly through communication module 330 via any known wireless communication means to a desired portion of the surgical console or system (not shown), such as, for example, via a dedicated wireless method such as Bluetooth Low Energy (BLE), Near Field Communications (NFC) or Wi-Fi technologies.

In an embodiment of the present invention, power to the phacoemulsification hand piece sensor module may be provided through a coin cell battery or like power source which may eliminate the need of cable 340. In such an embodiment, the lack of cable 340 may require use of wireless communications through communication module 330, as discussed above, and may allow for a less cumbersome use of the handpiece 20. In an embodiment, communication module 330 may be part of sensor module 320.

A steady and inflated anterior eye chamber may allow the surgeon to perform a more successful phacoemulsification procedure for cataract lens extraction and IOL insertion than otherwise possible with a high variance of pressure in the anterior chamber of the patient's eye. The pressure in the anterior chamber of the eye is a function of irrigation pressure, aspiration vacuum, and wound leakage. Variation of the anterior chamber pressure may come from the mismatch of sudden aspiration vacuum surge with unmet irrigation inflow, for example. The variation of the anterior chamber pressure causes instability and is not desirable during cataract lens extraction.

A typical method to provide a steady irrigation pressure is to hang a BSS bottle on an IV pole, or to pressurize the source BSS with additional pressure such as air or mechanical force, and connect the BSS via a tube to the irrigation port of the handpiece. The irrigation flow rate to the anterior chamber is then determined by the source pressure and the irrigation line resistance. The aspiration vacuum used may be generated by peristaltic pump or a Venturi vacuum source downstream from the handpiece aspiration port via a second tube. The aspiration vacuum level may be determined by the peristaltic vacuum setting, the Venturi vacuum setting, and/or one or more pressure or flow sensors. The aspiration vacuum may vary when operating in phacoemulsification mode when certain cataract material being removed from the anterior chamber partially or fully blocks the handpiece tip, also known as an occlusion event.

During an occlusion event, the vacuum continues to build up in the aspiration line, while the aspiration flow rate is reduced or stopped. Occasionally, the occlusion breaks free and the stored energy in the aspiration line is applied to the anterior chamber and suddenly pulls fluid from the anterior chamber resulting in a surge of outflow. When the irrigation inflow is substantially less than the aspiration out flow, the anterior chamber pressure will be less than steady state. More specifically, the anterior chamber pressure may be much lower than atmospheric pressure level, for example. Under such a condition, the anterior chamber may soften and become shallow, or in severe condition, may collapse.

In an embodiment of the present invention, methods for IOP management may include pressurized infusion, occlusion and post occlusion surge detection, and TOP control. More specifically, the present invention may utilize in-line irrigation and aspiration pressure sensors, as discussed above, to provide a more accurate and real-time measurement of system pressures nearer the surgical site. Such measurements, along with foot pedal position and bottle height (or specific irrigation pressure, for example), may provide inputs into certain algorithms (discussed in more detail herein) for control of system fractions.

Figure 4:
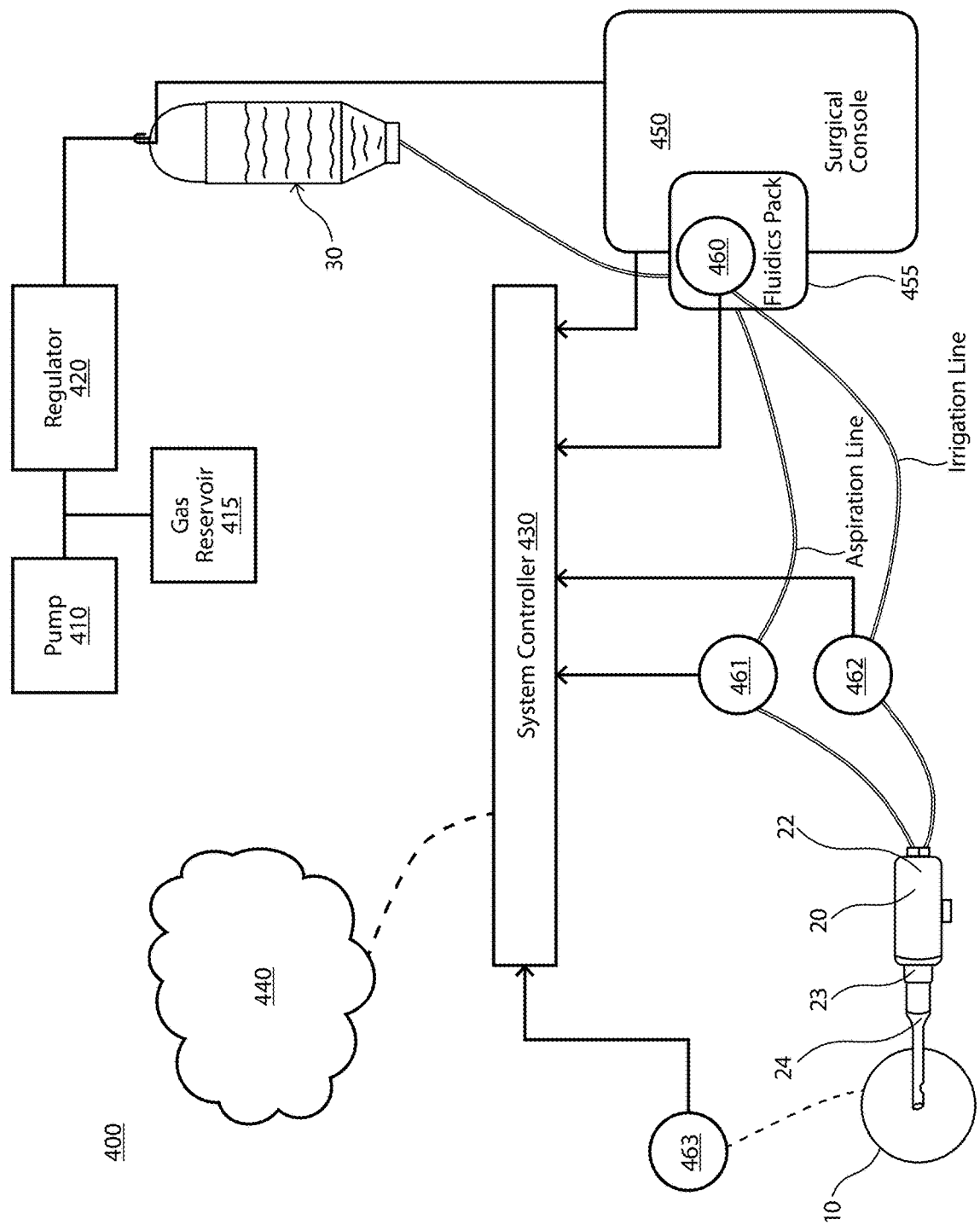
FIG. 4 illustrates an alternative phacoemulsification/diathermy/vitrectomy system and illustrated connected to various components of the system in order to determine characteristics or features of the components.

In an embodiment of the present invention, a plurality of pressure sensors may be used within a surgical system and may provide data which may be used to control aspects of the surgical system. A system level architecture and sensor placement of the present invention is illustrated in FIG. 4. In system 400, surgical console 450 may be in communication with irrigation source 30 and handpiece 20, for example. Surgical console 450 may also be in communication with pump 410, gas reservoir 415, and pressure regulator 420, each of which may be used for pressurized irrigation. Surgical console 450 may also be in communication with fluidics pack 455 and system controller 430, which may additionally be in communication with an intranet/internet 440.

Within system 400, an irrigation pressure sensor 462 may be located in close proximity to and/or be coupled to handpiece 20. Similarly, aspiration pressure/vacuum sensor 461 may be located in close proximity to and/or be coupled to handpiece 20. In an embodiment of the present invention, the aspiration pressure/vacuum sensor 461 may be used alone to provide substantially the same improvement in measurements. As described herein, the use of one or more pressure sensors may provide improved realtime measurements of patient eye level and wound leakage. For example, sensor 463 may be used to provided realtime measurements of eye 10.

The present invention provides various ways to overcome the negative effects of partial or full occlusions of the handpiece tip during phacoemulsification surgery. The systems and methods discussed herein may be further enhanced by better understanding the magnitude of an occlusion event. For example, existing methods only detect for one condition of occlusion without distinguishing weaker occlusion events from the stronger occlusion events. In addition, current system software do not provide a way to halt or break away from an occlusion event automatically. Instead, surgeons manually deal with occlusion events. As discussed above, occlusion is a state when the vacuum of aspiration passes a defined point of vacuum, referred to as the occlusion threshold, which may be selected near but below the maximum vacuum setting. During a strong or full occlusion, the vacuum may reach its max setting and aspiration will slow down significantly.

However, before the tip becomes near-fully occluded, a "weak occlusion" state occurs, where the aspiration is not at full speed but still active and operational. During a weak occlusion state, the surgeon may continue to break up the lens particles in an effective manner. Without the indication of a weak occlusion state, there may only be one threshold point, at a strong occlusion state, and the system may only notify the user when it detects a strong or full occlusion. For example, existing systems may divide the system vacuum into two parts based on the defined occlusion threshold. The first portion, or region, may start from the minimum vacuum setting to the user defined occlusion threshold point and is called the "normal state". The second region may start from the user defined occlusion threshold point and end at the selected max vacuum and is called the "occlusion state".

Typically, settings for system power, aspiration and pump ramp are selected for each state. These settings apply less power in the occlusion state. When the system is in an occlusion state, the surgeon may attempt to exit the occlusion state either through releasing of the foot-pedal controller (which controls, in part, the pressure of the system) or may use a variety of manual skills to ease or break away from the occlusion itself. Since the general method of occlusion detection is limited to detection of strong or full occlusions based on one threshold value, the surgeon may exit from the occlusion event prematurely to avoid generating unwanted heat by the active portion of the phacoemulsification handpiece tip when the aspiration approaches zero. However, adding the ability and confidence to operate in a weak occlusion state may provide a means to allow the surgeon to continually operate and break up the subject lens since aspiration is still active while vacuum and power are being suitably provided, further providing additional levels of safety to the system and possibly limiting the manual foot-pedal activities by the surgeon.

Figure 5A:
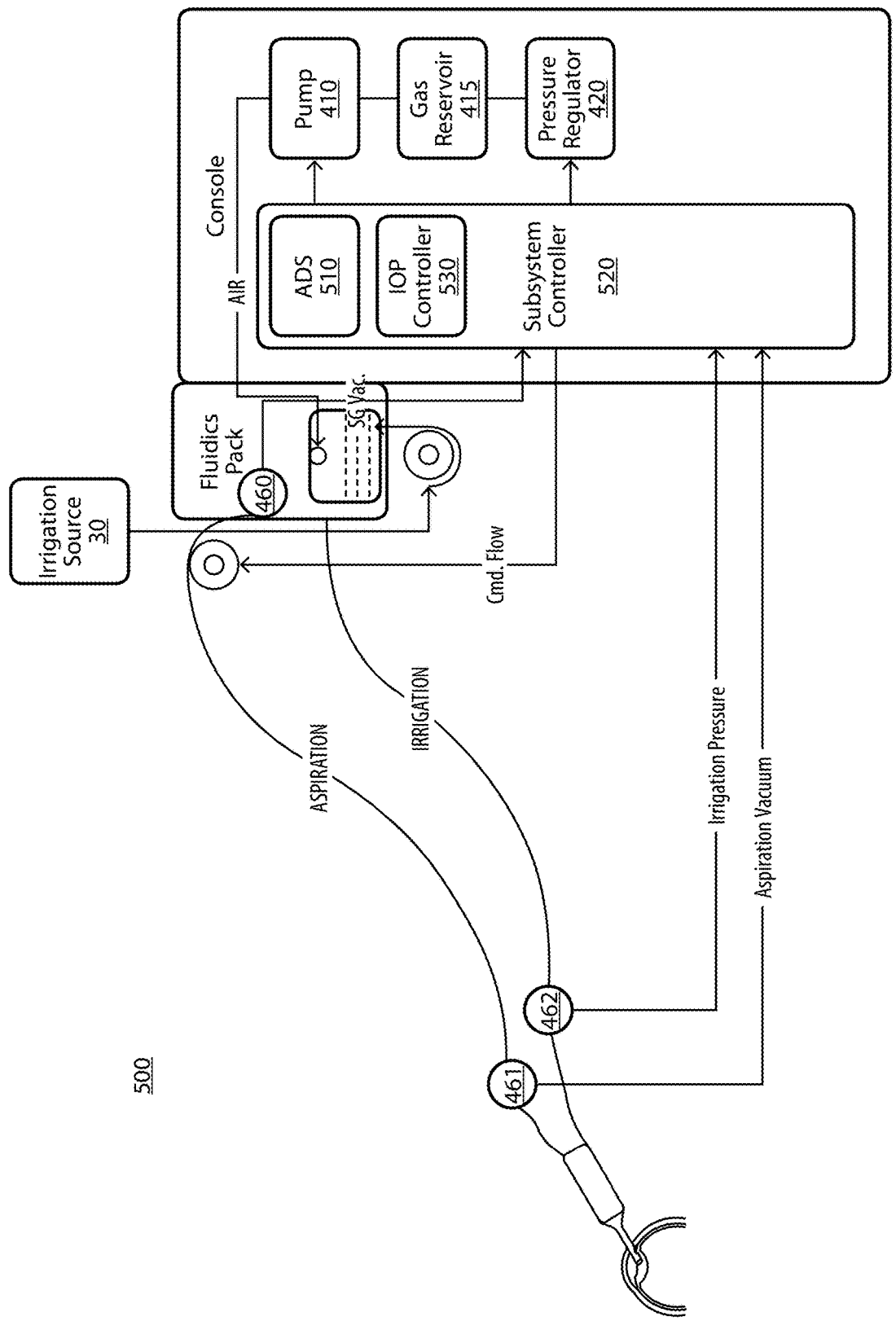
FIG. 5A illustrates an alternative phacoemulsification/diathermy/vitrectomy system and illustrated connected to various components of the system in order to determine characteristics or features of the components.
Figure 5B:
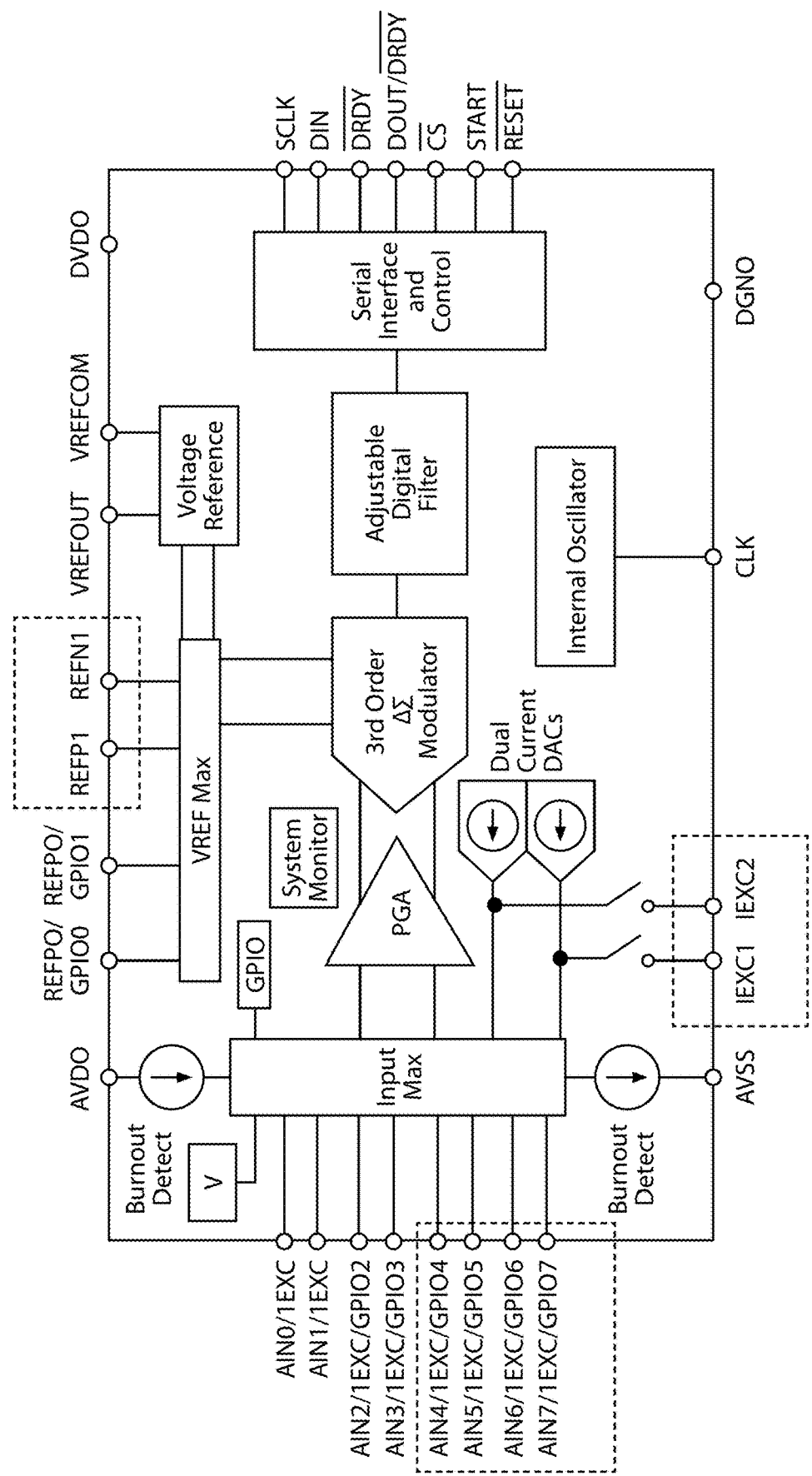
FIG. 5B illustrates circuitry associated with an embodiment of the present invention.

As illustrated in FIG. 5A, the intraoperative pressure management algorithm, which may be resident in surgical console 450, and, more particularly, within subsystem controller 520, may receive sensor data from the analog to digital converter (ADS) 510, and may continuously measure and adjust the irrigation pressure of system 400 through the TOP management controller 530, in order to maintain the anterior chamber pressure within certain intraoperative parameters. An exemplary ADS for use with system 500 is illustrated in FIG. 5B. By way of non-limiting example, the intraoperative pressure management algorithm my account for a drop in the anterior chamber pressure due to fluid out flow when the surgeon begins to aspirate fluid by pressing on a foot pedal controller (not shown). The TOP management controller 530 may control the pump 410, a gas reservoir 415, the pressure regulator 420, and the height of irrigation source 30.

Figure 6:
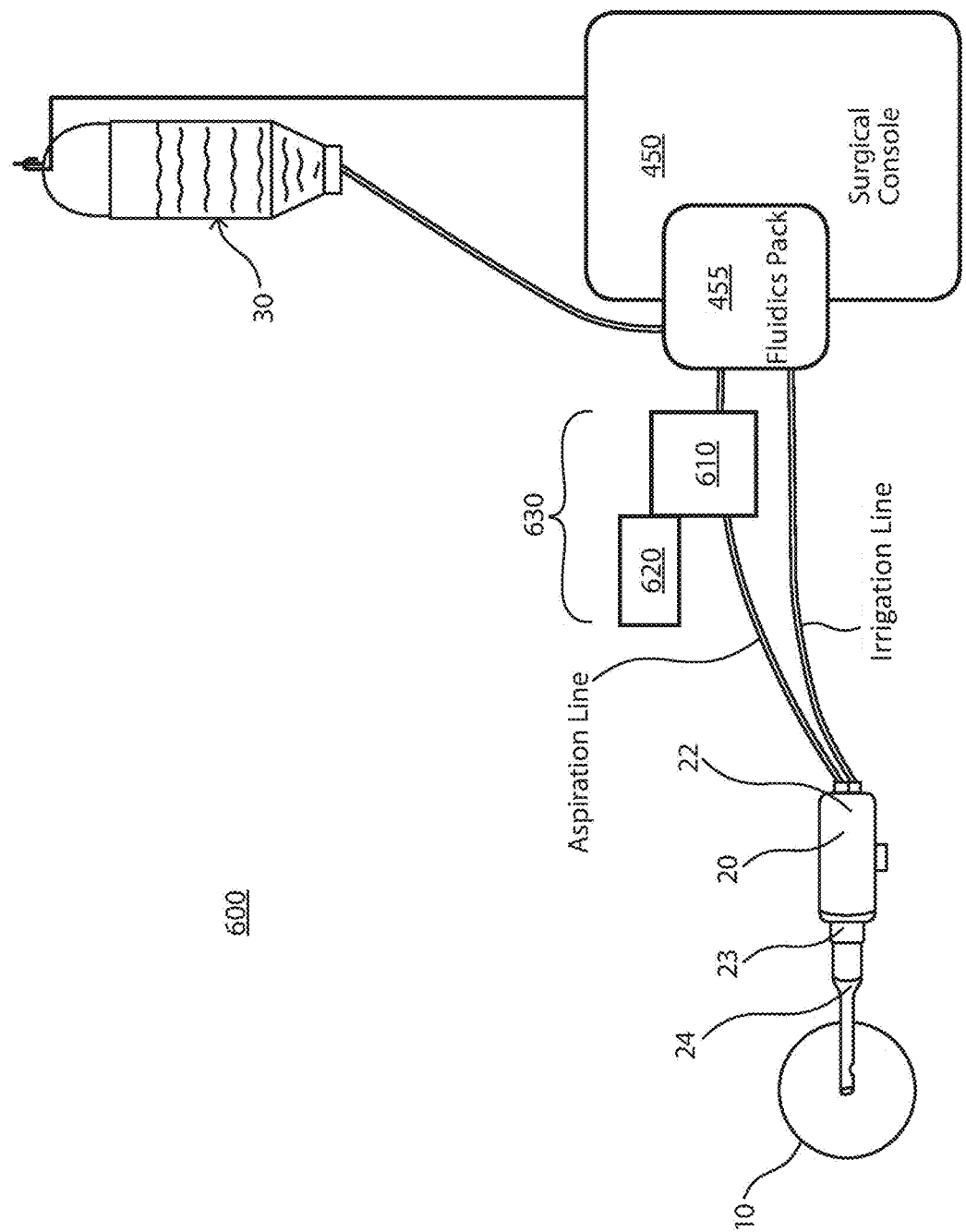
FIG. 6 illustrates an alternative phacoemulsification/diathermy/vitrectomy system and illustrated connected to various components of the system in order to determine characteristics or features of the components.

FIG. 6 illustrates an alternative phacoemulsification/diathermy/vitrectomy system 600. The reduced pressure mechanism 630 may be located at any point along irrigation line 32 between the irrigation source 30 and the handpiece 20. An in-line check valve (not shown) in series and between reduced pressure mechanism 630 and irrigation source 30 may ensure that pressured fluid moves towards the handpiece 20 and may also prevent fluid back flow from the anterior chamber toward the irrigation source 30 when the mechanism retracts from the activated position to deactivated position, for example. Reduced pressure mechanism 630 may be a single, unitary device, such as a direct action actuator which may exert pressure on the irrigation line 32 by using a plunger or other like apparatus to reduce the interior diameter of the irrigation line 32 sufficiently to force a quantity of irrigation fluid forward through the handpiece 20 into the eye 10. As discussed above, sensors associated with the present invention may allow the surgical console 450 to track and monitor pressure changes associated with occlusions and may activate reduce pressure mechanism 630 as necessary to maintain a desired pressure in the eye 10, and, more specifically, in the anterior chamber of eye 10.

Reduced pressure mechanism 630 may also be composed of multiple parts. For example, reduced pressure mechanism 630 may include an actuation mechanism 620 and a compensation volume module 610. The inclusion of a compensation volume module 610 may allow for an increased volume of irrigation fluid available to the reduced pressure mechanism 630. For example, compensation volume module 610 may include additional amounts of irrigation line 32 which may be acted upon by actuation mechanism 620. Such an increased amount of line may be accommodated by looping the line in a circular pattern and/or weaving the line in a serpentine manner. In any embodiment of line aggregation, those skilled in the art will recognize the various adaptations of actuators and plunger like formations may be made suitable to in part a desired force on at least a portion of the aggregated irrigation line. Similarly, in an embodiment of the present invention, compensation volume module 610 may include a reservoir of irrigation fluid which may be introduced into irrigation line 32 as necessary to create or augment an increase in pressure. In an embodiment of the present invention, the reduced pressure mechanism 630 and/or in-line check valve 460 may be incorporated into fluid pack 455. In an embodiment of the present invention, fluid pack 455 may be in the form of a cassette which may be removably attached to surgical console 450 and may include at least one reduced pressure mechanism 630 and/or at least one in-line check valve 460.

In an embodiment of the present invention, the amount of momentary fluid pressure and the duration of time the applying time of the irrigation source may be adjusted by the reduced pressure mechanism 630 with the amount of pressure and time related to the compensation volume and the speed of the mechanism.

Figure 7A:
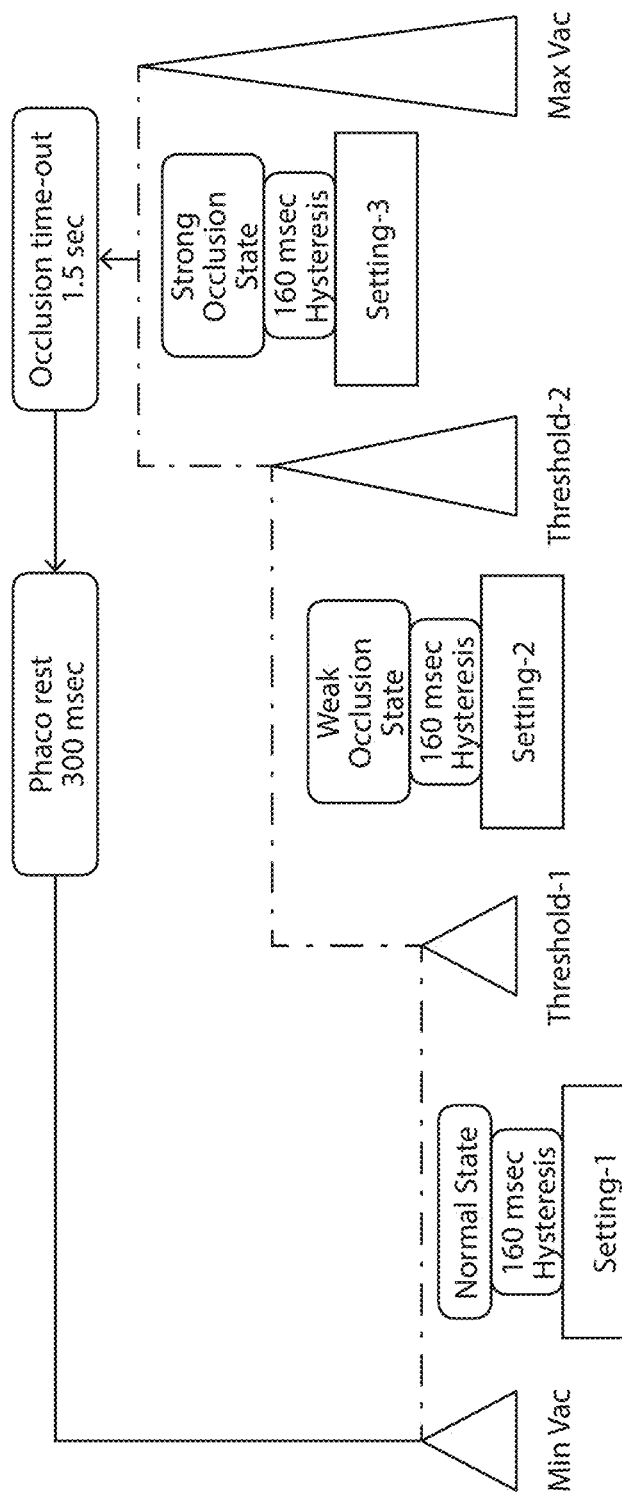
FIG. 7A is a block diagram illustrative of an embodiment of the present invention.

In an embodiment of the present invention, the vacuum provided by the system may be defined by at least three regions, each region having its own settings for power, pressure, and pressure threshold. For example, in a three region embodiment, the regions may be, the "normal state" or un-occluded, the "weak occlusion state," and the "strong occlusion state." As illustrated in FIG. 7A, in a three region embodiment, the user may define two thresholds instead of one related to occlusion events. The first threshold may separate the un-occluded state from an at least partially occluded state. The second threshold may divide the occluded state into two separate states, a weak occlusion state and a strong occlusion state. Each region may carry unique settings and parameters which may include, but is not limited to, power, aspiration, pump ramp, and sound. In an embodiment, the settings and parameters may be user selectable before and/or during a surgery, e.g. power level, aspiration rate, pump ramp rate, and/or sound level.

In an embodiment of the present invention, hysteresis may be applied to each region during operation to avoid frequent switching between the regions. For example, each state may have a minimum time delay in that state before switching to next state once a threshold has been crossed. A minimum time delay may be set by the user to any timing desired, and may be between about 120 msec to about 200 msec, and may preferably be a fixed delay of 160 msec between each state. A minimum time delay may also reduce trafficking of vacuum values to the hardware which may slow reaction time. Although thresholds may be selected by the user, it is preferable that the second threshold should be larger or the same as first threshold.

Being provided with a more refined division of an occlusion event may allow a surgeon to operate within, for example, the weak occlusion state for a longer period of time without worrying about the heat or inactivity of aspiration generally accompanied in the strong occlusion state. In addition, the surgeon may want to apply a strong power setting in the weak occlusion state to be more productive in breaking up the lens and aspirating the particles so as to avoid a strong occlusion state altogether.

For the last divided region, most often the strong occlusion state, the handpiece tip may be substantially or fully occluded. Once in the strong occlusion state, rather than having the surgeon manually release the aspiration pressure through a foot pedal command, for example, or by simply removing the handpiece from the surgical site, an automated behavior may be implemented to better handle this state. In an embodiment of the present invention, and as illustrated in FIG. 7A, a time limit may be applied in the settings of the strong occlusion state to time out the system vacuum before automatically exiting the strong occluded state. Such a time limit may be, for example, 1.5 seconds. Exiting the strong occlusion state by temporarily disabling the "Phaco" mode or lowering the setting for a short period (300 msec) may allow the power, vacuum, and aspiration to approach or achieve zero which may allow for the release of the occluded particle (meaning that the particle may be loosened and/or freed from the handpiece tip so as not to be stuck in an occluded state) before the system can re-apply the settings to resume Phaco mode, for example. Although the "time-out" for an occlusion break is selectable, a default of 1.5 seconds is preferable for breaking the occlusion state.

This aspect of the present invention may provide increased operational flexibility and an improved method for the break up and removal of lens particles. Similarly, the use of a "time-out" in the strong occlusion state may closely mimic the manual action of releasing and then pushing down the foot-pedal associated with the surgical system, but in an automated and much quicker fashion and no need for the surgeon to constantly press and release the foot-pedal to deal with occlusion. Although not shown in FIG. 7A, the occlusion states may be broken into more than two different states and may, for example, include three occlusion states in addition to a first "normal state." Similarly, various states may buttress the "normal" operation state in accordance with the needs of the surgical console user.

As shown in the chart of FIG. 7B, a certain level of power may be associated with each state. For example, the normal state may have a max power of 35% a max aspiration of 20 ccm and be in the vacuum range of 0 to about 246 mmHg, the weak occlusion state may have a max power of 55% a max aspiration of about 45 ccm and be in the vacuum range of about 246 to about 370 mmHg, and the strong occlusion state may have a max power of 45% and a max aspiration of about 30 ccm and be in the vacuum range of about 370 to about 390 mmHg, for example. The time spent by the system in any given state may be a function of the vacuum threshold set and may be variable given the size and type of occlusion encountered. In an embodiment of the present invention, hysteresis may be applied to each region which may ensure a minimum time in the given state before switching to a next state. The present invention may be applied to the existing methods using two state occlusion regions or a plurality of state occlusion regions. In an embodiment of the present invention, and in accordance with the teachings above, a graphical user interface may display conservative, moderate and aggressive modes, and the like, correspondent to each mode selection. During use, for example, in each mode, the occlusion state may determine what percentage of maximum aspiration, vacuum and power settings to apply.

Figure 7C:
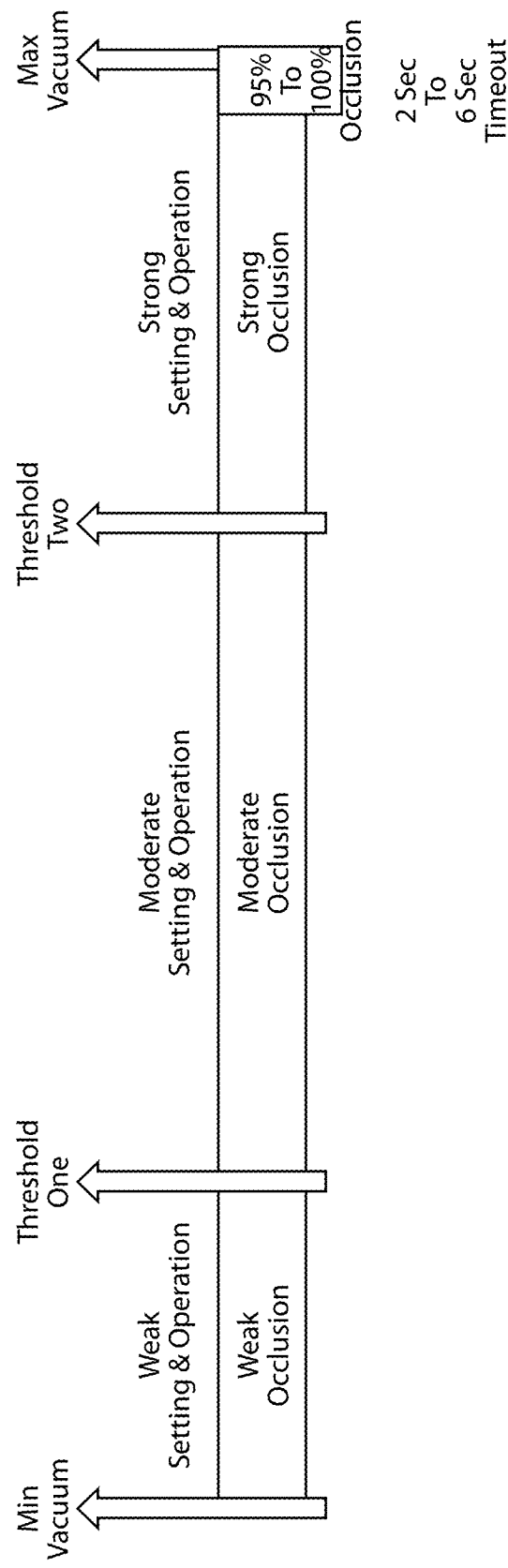
FIG. 7C is a chart illustrative of an embodiment of the present invention.

In an embodiment of the present invention, different settings such as, for example, power, power modalities, aspiration, and pump ramp based on real vacuum produced by the system may be applied. As illustrated in FIG. 7C, when, for example, the real vacuum is between Min Vacuum and Threshold One, a negligible power and/or other weak setting may be applied to save energy. When the real vacuum or measured vacuum is between Threshold One and Threshold Two, a moderate setting with a moderate power may be applied. When the real vacuum or measured vacuum is between Threshold Two and Max Vacuum, then a strong setting with a strong power may be applied to produce strong operation. Similarly, if as a result of an occlusion the real vacuum or measured vacuum approaches or achieves a maximum vacuum (e.g. 95% to 100%), then a timer may limit the imposed condition, e.g. length of time the power is applied at the particular setting strength, e.g. strong power setting/operation.

By way of non-limiting example only, an imposed variable time may be reversely proportional to the occlusion percent. For example, at 100% occlusion, the variable time limit may be a minimum of 2 seconds, while at 95% occlusion, the variable time limit may be a maximum of 6 seconds. After at least one timeout, Power, Vacuum and/or Aspiration may be removed temporarily for a period of time sufficient to release particles at the handpiece. Such a period of time may be, for example, up to 300 milliseconds. The system may reset after a timeout and start at a minimum vacuum, for example. Hysteresis, as further described herein, may be applied when switching from one setting to another.

Figure 8:
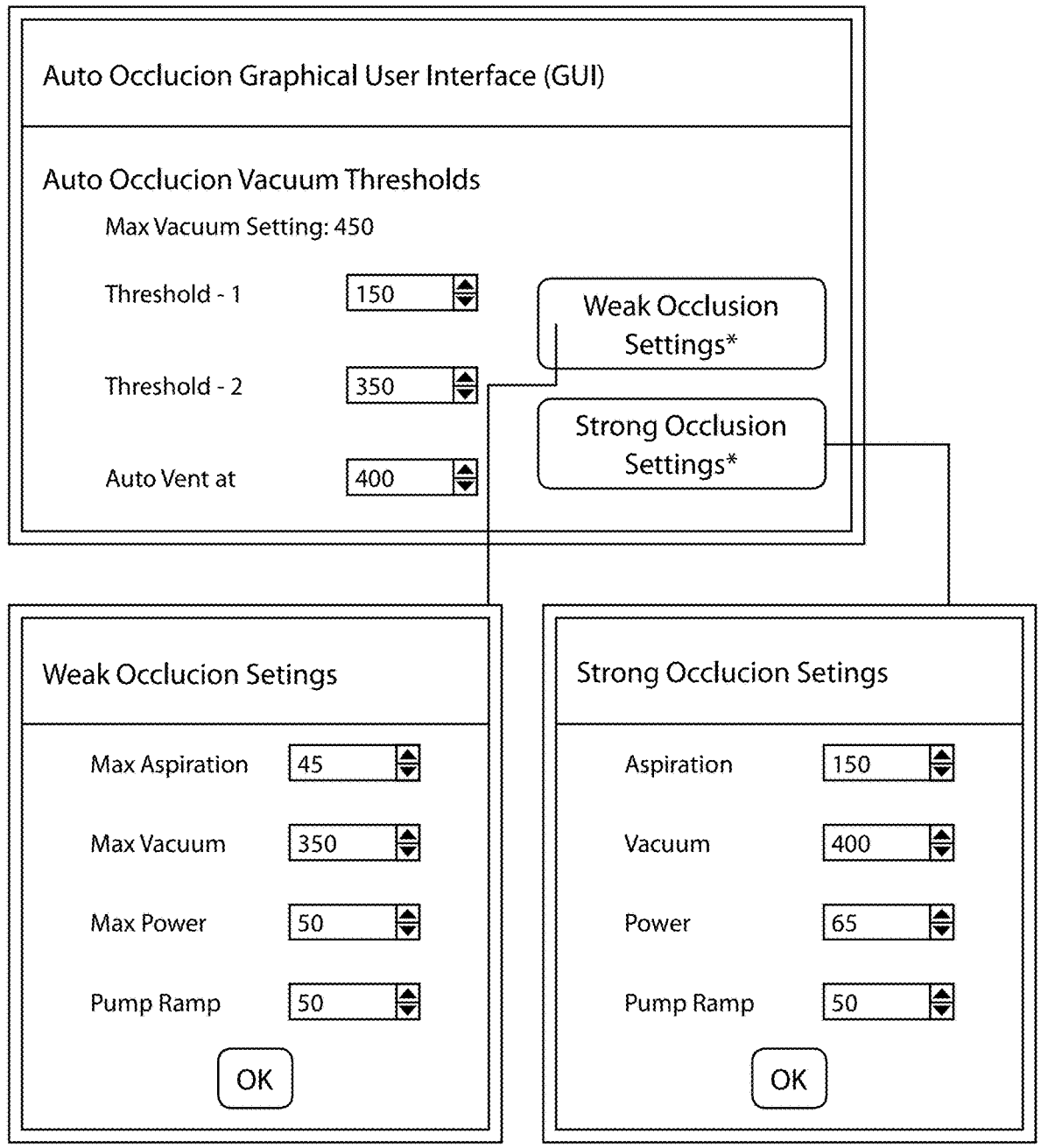
FIG. 8 is an exemplary graphical user interface in accordance with at least one embodiment of the present invention.

As shown in the exemplary graphical user interface (GUI) of FIG. 8, the GUI provides options to enable a user of the system to define system settings. For example, in one implementation, a user may define weak occlusion settings and strong occlusion settings. Weak occlusion settings may include, but is not limited to, max aspiration, max vacuum, max power, and pump ramp settings. Strong occlusion settings may include, but is not limited to, aspiration, vacuum, power, and pump ramp settings. In another embodiment, a user may define auto occlusion thresholds only. In this embodiment, a software algorithm may be utilized to automatically calculate settings to best fit weak occlusion behavior and strong occlusion behavior. Auto occlusion vacuum threshold settings may include, but is not limited to, threshold vacuum settings 1 and 2 and an auto vent setting.

Figure 9:
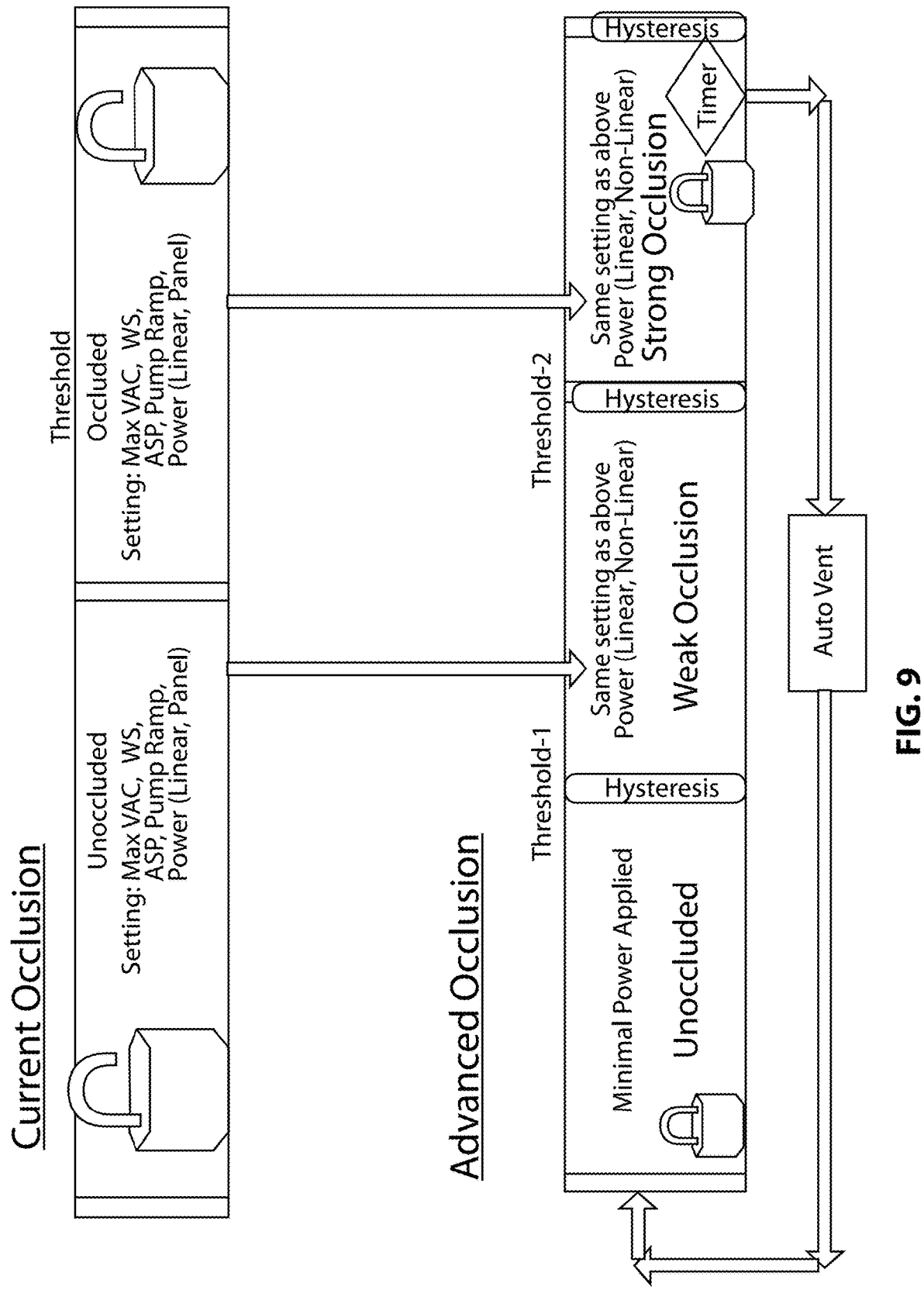
FIG. 9 is an exemplary graph comparing current occlusion to advanced occlusion in accordance with at least one embodiment of the present invention.

A comparison diagram is shown in FIG. 9 in accordance with at least one embodiment. A comparison is shown between current occlusion and advanced occlusion. Two thresholds may be introduced to divide a max vacuum into three sections. The three sections may be A) unoccluded, B) weak occluded, and C) strong occluded. The sections with weak occluded and strong occluded may be assigned a setting much like current occlusion. The unoccluded section may be assigned a minimum power setting, such as a minimal pulse like auto Phaco. Hysteresis is a safety feature in the event of a transition from one state to another with a certain delay. Auto Vent is a safety feature to prevent the generation of heat when occlusion approaches a max vacuum level and continues or exceeds for a certain period of time.

Figure 10:
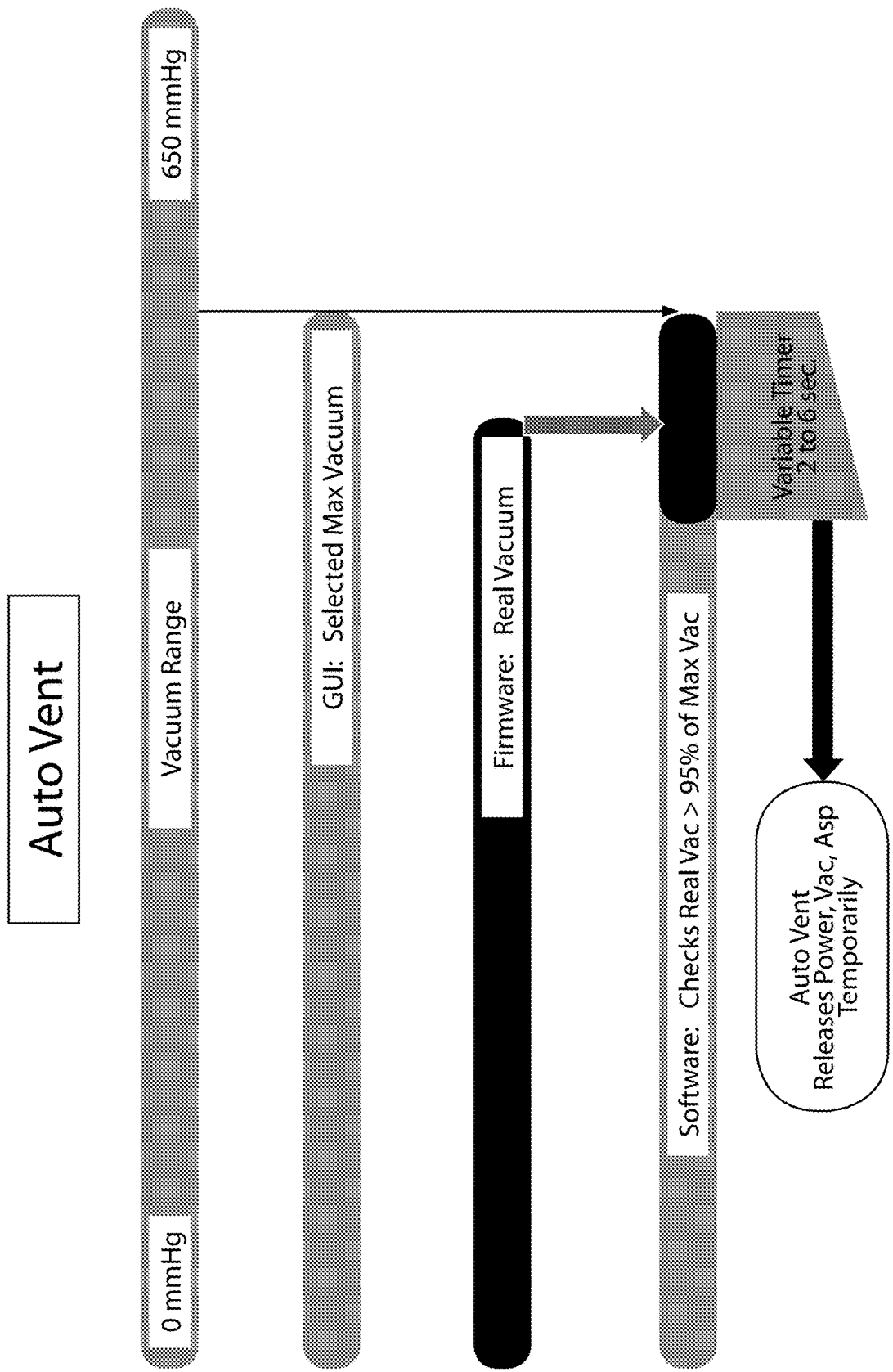
FIG. 10 is an exemplary graph displaying auto vent in accordance with at least one embodiment of the present invention.

In accordance with FIG. 10, shown is a diagram for the Auto Vent feature. As mentioned above, Auto Vent is a safety feature to prevent the generation of heat when occlusion approaches a max vacuum level and continues or exceeds for a certain period of time. In an exemplary embodiment, when the vacuum exceeds 95% of max vacuum continuously for a certain period of time (i.e. 2 to 6 seconds, the higher real vacuum, the lower time), then Auto Vent may be activated. The Auto Vent process may be executed by firmware and may take around 250 msec. After completion, the system goes back to normal. The Auto Vent may release the particle at handpiece tip and aspiration, vacuum, and power start fresh.

A method for managing occlusions during phacoemulsification surgery may comprise providing, by a surgical console having at least one system bus communicatively connected to at least one computing processor capable of accessing at least one computing memory associated with the at least one computing processor, a vacuum system capable of providing vacuum pressure between a minimum pressure and a maximum pressure. The method may further comprise receiving a first pressure threshold setting and a second pressure threshold setting, wherein the first pressure threshold setting is greater than the minimum pressure and less than the second pressure threshold setting and wherein the second pressure threshold setting is less than the maximum pressure. A user of the surgical console may be provided with an alert in response to the vacuum pressure being greater than the first pressure threshold setting. The vacuum pressure may be automatically reduced in response to the second pressure threshold setting being exceeded.

In an embodiment, the first pressure threshold setting may be selected greater than zero mmHg but less than the maximum pressure. The second pressure threshold setting may b e selected from a range consisting of any value equal to or greater than threshold one but less than the maximum pressure. The maximum pressure may be selected from a range consisting of any value greater than zero mmHg to about 650 mmHg. The automatically reducing of the vacuum pressure may begin when the vacuum pressure exceeds 95% of the maximum pressure setting in over 2 seconds. The automatically reducing of the vacuum pressure may reduce the demand vacuum to about the minimum pressure. The automatically reducing of the vacuum pressure may reduce the demand vacuum to about the minimum pressure for a predetermined delay. The automatically reducing of the demand vacuum may reduce the vacuum pressure to about the minimum pressure for less than 300 msec. The automatically reducing of the vacuum pressure may reduce the demand vacuum to less than the first pressure threshold setting. The automatically reducing of the vacuum pressure may result in a temporary disabling of a surgical tool associated with the surgical console. Hysteresis may be used to determine if a threshold is exceeded.

A system for managing occlusions during phacoemulsification surgery may comprise a surgical console having at least one system bus communicatively connected to at least one computing processor capable of accessing at least one computing memory associated with the at least one computing processor. The system may further comprise at least one vacuum source associated with the surgical console for providing a vacuum pressure between a minimum pressure and a maximum pressure and a phacoemulsification surgical handpiece having at the distal end at least one surgical tool and having near the proximate end a receiver for receiving an aspiration line from the surgical console. The system may further comprise an input means for receiving a first pressure threshold setting and a second pressure threshold setting. The first pressure threshold setting may be greater than the minimum pressure and less than the second pressure threshold setting. The second pressure threshold setting may be less than the maximum pressure.

The first pressure threshold setting may be selected from a range consisting of about 5 mmHg to about the maximum pressure setting minus 5 mmHg. The second pressure threshold setting may be selected from a range consisting of about the first threshold to about the maximum pressure setting minus 5 mmHg. The maximum pressure may be selected from a range consisting of about 5 mmHg to about 650 mmHg. The automatically reducing of the vacuum pressure may occur less than from 2 seconds to 6 seconds, when the real pressure goes above 95% of the pressure setting. The input means may comprise a graphical user interface. The surgical tool may comprise a needle.

A system for managing occlusions during phacoemulsification surgery may comprise a surgical console having at least one system bus communicatively connected to at least one computing processor capable of accessing at least one computing memory associated with the at least one computing processor and at least one vacuum source associated with the surgical console for providing a vacuum pressure between a minimum pressure and a maximum pressure. The system may further comprise a phacoemulsification surgical handpiece having at a distal end at least one surgical tool and having at a proximate end a receiver for receiving an aspiration line from the surgical console. The system may further comprise an input means for receiving a plurality of pressure threshold settings. In an embodiment, ones of the plurality of pressure threshold settings are greater than the minimum pressure and less than the maximum pressure.

The ones of the plurality of pressure threshold settings is selected from a range consisting of about 5 mmHg to about the maximum pressure setting. The ones of the plurality of pressure threshold settings may be selected from a range consisting of about 5 mmHg to ab out 650 mmHg. The automatically reducing of the vacuum pressure may occur less from 2 seconds to 6 seconds when the real pressure goes above 95% of the pressure setting. The vacuum pressure may be reduced to zero mmHg. The vacuum pressure may be reduced to zero mmHg from about 2 seconds to about 6 seconds. The input means may comprise a graphical user interface. The at least one surgical tool may comprise a needle.

A method for managing occlusions during phacoemulsification surgery may comprise providing through a surgical instrument a first vacuum pressure and receiving an indication of at least a partial occlusion based on a second vacuum pressure that is greater than the first vacuum pressure. The method may further comprise providing through the surgical instrument a change of one or more parameters from the group consisting of power level, aspiration rate, pump ramp rate, and sound level, in accordance with the indication. In an embodiment, a second indication of a strong occlusion may be received based on a third vacuum pressure that is greater than the second vacuum pressure. A change of one or more parameters may be provided through the surgical instrument from the group consisting of power level, aspiration rate, pump ramp rate, and sound level, in accordance with the second indication. The first pressure may be zero mmHg. The change of parameters as a result of the indication may remain for a preset amount of time.

A method for managing occlusions during phacoemulsification surgery may comprise providing, by a surgical console having at least one system bus communicatively connected to at least one computing processor capable of accessing at least one computing memory associated with the at least one computing processor, a vacuum system comprising three regions capable of providing vacuum pressure between a minimum pressure and a maximum pressure. The method may further comprise receiving a first pressure threshold setting and a second pressure threshold setting. The first pressure threshold setting may be greater than the minimum pressure and less than the second pressure threshold setting. The second pressure threshold setting may be less than the maximum pressure. A graphical user interface may display current aspiration, vacuum, and power settings. Three regions capable of providing vacuum pressure may be normal state, weak occlusion state, and strong occlusion state. Each of the three regions may possess respective settings comprising power level, pressure, and pressure threshold. The normal state may be between the minimum pressure and the first pressure threshold, the weak occlusion state may be between the first pressure threshold and the second pressure threshold, and the strong occlusion state may be between the second pressure threshold and the maximum pressure. The normal state may be in a vacuum pressure range of 0 mmHg and the first pressure threshold. The weak occlusion state may be in a vacuum pressure range of the first pressure threshold to the second pressure threshold. The strong occlusion state may be in a vacuum pressure range of the second pressure threshold to the maximum selected pressure. The power level for each of the three regions is programmed. The power level is a range of power levels. The power level for each of the three regions is programmed by a user prior to the phacoemulsification surgery. The normal state has a selectable power level range between 0% to 10%. The weak occlusion state has a selectable power level range between 20% to 60%. The strong occlusion state has a selectable power level range between 1% to 100%. An amount of time spent by the system in one of the three regions is a function of the vacuum pressure threshold for the given region. A minimum amount of time spent by the system in each region before switching to a different state is preprogrammed.

The previous description is provided to enable any person skilled in the art to make or use the disclosed embodiments. Various modifications to these embodiments will be readily apparent to those skilled in the art, and the generic principles defined herein may be applied to other embodiments without departing from the spirit or scope of the invention. Thus, the present disclosure is not intended to be limited to the embodiments shown herein but is to b e accorded the widest scope consistent with the principles and novel features disclosed herein.

The invention claimed is:

1. A method for managing occlusions during phacoemulsification surgery, the method comprising:
providing, by a surgical console having at least one system bus communicatively connected to at least one computing processor capable of accessing at least one computing memory associated with the at least one computing processor, a vacuum system capable of providing vacuum pressure between a minimum pressure and a maximum pressure;
receiving a first pressure threshold setting and a second pressure threshold setting, wherein the first pressure threshold setting is greater than the minimum pressure, the second pressure threshold setting is greater than the first pressure threshold setting, and the second pressure threshold setting is less than the maximum pressure;
providing a user of the surgical console a non-visual alert in response to the vacuum pressure being greater than the first pressure threshold setting; and
automatically reducing the vacuum pressure in response to the second pressure threshold setting being exceeded, wherein the non-visual alert is provided before automatically reducing the vacuum pressure.

2. The method of claim 1, wherein the first pressure threshold setting is selected greater than zero mmHg but less than the maximum pressure.

3. The method of claim 1, wherein the maximum pressure is selected from a range comprising any value greater than zero mmHg to about 650 mmHg.

4. The method of claim 1, wherein the automatically reducing of the vacuum pressure begins when the vacuum pressure exceeds 95% of the maximum pressure for over 2 seconds.

5. The method of claim 1, wherein the automatically reducing of the vacuum pressure reduces the vacuum pressure to about the minimum pressure.

6. The method of claim 1, wherein the automatically reducing of the vacuum pressure reduces the vacuum pressure to about the minimum pressure for a predetermined delay, wherein the predetermined delay is greater than zero seconds.

7. The method of claim 1, wherein the automatically reducing of the vacuum pressure reduces the vacuum pressure to about the minimum pressure for less than 300 msec.

8. The method of claim 1, wherein the automatically reducing of the vacuum pressure reduces the vacuum pressure to less than the first pressure threshold setting.

9. The method of claim 1, wherein the automatically reducing of the vacuum pressure results in a temporary disabling of a surgical tool associated with the surgical console.

10. The method of claim 1, wherein hysteresis is used to determine if the first pressure threshold setting is exceeded or if the second pressure threshold setting is exceeded.

11. The method of claim 1, wherein the non-visual alert only occurs when the vacuum pressure is greater than the first pressure threshold setting.

12. A system for managing occlusions during phacoemulsification surgery, the system comprising:
a surgical console having at least one system bus communicatively connected to at least one computing processor capable of accessing at least one computing memory associated with the at least one computing processor;
at least one vacuum source associated with the surgical console for providing a vacuum pressure between a minimum pressure and a maximum pressure;
a phacoemulsification surgical handpiece having at a distal end at least one surgical tool and having at a proximate end a receiver for receiving an aspiration line from the surgical console; and
an input device for receiving a first pressure threshold setting and a second pressure threshold setting, wherein the first pressure threshold setting is greater than the minimum pressure, the second pressure threshold setting is greater than the first pressure threshold setting, and the second pressure threshold setting is less than the maximum pressure,
wherein the surgical console provides a user of the surgical console a non-visual alert when the vacuum pressure is greater than the first pressure threshold setting, wherein the non-visual alert is provided before the vacuum pressure is automatically reduced.

13. The system of claim 12, wherein the first pressure threshold setting is selected from a range comprising about 5 mmHg to about the maximum pressure minus 5 mmHg.

14. The system of claim 12, wherein the second pressure threshold setting is selected from a range comprising about the first pressure threshold setting to about the maximum pressure minus 5 mmHg.

15. The system of claim 12, wherein the maximum pressure is selected from a range comprising about 5 mmHg to about 650 mmHg.

16. The system of claim 12, further comprising:
the at least one computer processor configured to automatically reduce the vacuum pressure in response to the second pressure threshold setting being exceeded.

17. The system of claim 12, wherein the input device comprises a graphical user interface.

18. The system of claim 12, wherein the surgical tool comprises a needle.

19. The system of claim 12, wherein the non-visual alert only occurs when the vacuum pressure is greater than the first pressure threshold setting.

20. A system for managing occlusions during phacoemulsification surgery, the system comprising:
a surgical console having at least one system bus communicatively connected to at least one computing processor capable of accessing at least one computing memory associated with the at least one computing processor;
at least one vacuum source associated with the surgical console for providing a vacuum pressure between a minimum pressure and a maximum pressure;
a phacoemulsification surgical handpiece having at a distal end at least one surgical tool and having at a proximate end a receiver for receiving an aspiration line from the surgical console; and
an input device for receiving a plurality of pressure threshold settings, wherein the plurality of pressure threshold settings are greater than the minimum pressure and less than the maximum pressure,
wherein the surgical console provides a user of the surgical console a non-visual alert when the vacuum pressure is greater than a first pressure threshold setting of the plurality of pressure threshold settings, wherein the non-visual alert is provided before the vacuum pressure is automatically reduced.

21. The system of claim 20, wherein the plurality of pressure threshold settings are selected from a range comprising about 5 mmHg to about the maximum pressure.

22. The system of claim 20, wherein plurality of pressure threshold settings are selected from a range comprising about 5 mmHg to about 650 mmHg.

23. The system of claim 20, further comprising:
automatically reducing the vacuum pressure in response to a pressure threshold setting of the plurality of pressure threshold settings being exceeded.

24. The system of claim 20, wherein the vacuum pressure is reduced to zero mmHg.

25. The system of claim 20, wherein the vacuum pressure is reduced to zero mmHg from about 2 seconds to about 6 seconds.

26. The system of claim 20, wherein the input device comprises a graphical user interface.

27. The system of claim 20, wherein the non-visual alert only occurs when the vacuum pressure is greater than the first pressure threshold setting of the plurality of pressure threshold settings.

28. The system of claim 20, wherein the at least one surgical tool comprises a needle.

29. A method for managing occlusions during phacoemulsification surgery, the method comprising:
providing through a surgical instrument a first vacuum pressure;
receiving a non-visual indication of a partial occlusion based on a second vacuum pressure that is greater than the first vacuum pressure; and
providing through the surgical instrument a change of one or more parameters from the group consisting of pump ramp rate and sound level, in accordance with the non-visual indication,
wherein the non-visual indication is provided before the change of one or more parameters.

30. The method of claim 29, further comprising receiving a second indication of a strong occlusion based on a third vacuum pressure that is greater than the second vacuum pressure; and
providing through the surgical instrument a change of one or more parameters from the group consisting of power level, aspiration rate, pump ramp rate, and sound level, in accordance with the second indication.

31. The method of claim 29, wherein the first vacuum pressure is zero mmHg.

32. The method of claim 29, wherein the change of parameters as a result of the indication remain for a preset amount of time.

33. The method of claim 29, wherein the non-visual indication only occurs when the vacuum pressure is greater than the first vacuum pressure.

34. A method for managing occlusions during phacoemulsification surgery, the method comprising:
providing, by a surgical console having at least one system bus communicatively connected to at least one computing processor capable of accessing at least one computing memory associated with the at least one computing processor, a vacuum system comprising three regions capable of providing a vacuum pressure between a minimum pressure and a maximum pressure;
receiving a first pressure threshold setting and a second pressure threshold setting, wherein the first pressure threshold setting is greater than the minimum pressure, the second pressure threshold setting is greater than the first pressure threshold setting, and the second pressure threshold setting is less than the maximum pressure;
displaying, on a graphical user interface, current aspiration, vacuum, and power settings; and
providing a non-visual notification to an operator when the vacuum pressure is greater than the first pressure threshold setting;
wherein the three regions capable of providing vacuum pressure are normal state, weak occlusion state, and strong occlusion state;
wherein each of the three regions possess respective settings comprising power level, pressure, and pressure threshold;
wherein the normal state is between the minimum pressure and the first pressure threshold setting, the weak occlusion state is between the first pressure threshold setting and the second pressure threshold setting, and the strong occlusion state is between the second pressure threshold setting and the maximum pressure; and
wherein the non-visual notification is provided before the strong occlusion state.

35. The method of claim 34, wherein the normal state is in a vacuum pressure range of zero mmHg and the first pressure threshold.

36. The method of claim 34, wherein the vacuum system is operational in the weak occlusion state.

37. The method of claim 34, wherein the power level for each of the three regions is programmed.

38. The method of claim 37, wherein the power level is a range of power levels.

39. The method of claim 34, wherein the power level for each of the three regions is programmed by a user prior to the phacoemulsification surgery.

40. The method of claim 37, wherein the normal state has a selectable power level range between 0% to 10%.

41. The method of claim 37, wherein the weak occlusion state has a selectable power level range between 20% to 60%.

42. The method of claim 37, wherein the strong occlusion state has a selectable power level range between 1% to 100%.

43. The method of claim 34, wherein an amount of time spent by the system in one of the three regions is a function of the vacuum pressure for the one of the three regions.

44. The method of claim 34, wherein a minimum amount of time spent by the system in each region before switching to a different state is preprogrammed.

45. The method of claim 34, wherein the non-visual notification only occurs when the vacuum pressure is greater than the first pressure threshold setting.

* * * * *